US010219944B2

(12) United States Patent
Tedford et al.

(10) Patent No.: US 10,219,944 B2
(45) Date of Patent: Mar. 5, 2019

(54) DEVICES AND METHODS FOR NON-INVASIVE MULTI-WAVELENGTH PHOTOBIOMODULATION FOR OCULAR TREATMENTS

(71) Applicant: LumiThera, Inc., Poulsbo, WA (US)

(72) Inventors: Clark E Tedford, Poulsbo, WA (US); Scott DeLapp, San Diego, CA (US); Scott Bradley, San Marcos, CA (US)

(73) Assignee: LumiThera, Inc., Poulsbo, WA (US)

( * ) Notice: Subject to any disclaimer, the term of this patent is extended or adjusted under 35 U.S.C. 154(b) by 342 days.

(21) Appl. No.: 14/849,581

(22) Filed: Sep. 9, 2015

(65) Prior Publication Data

US 2016/0067086 A1   Mar. 10, 2016

Related U.S. Application Data

(60) Provisional application No. 62/048,182, filed on Sep. 9, 2014, provisional application No. 62/048,187, filed on Sep. 9, 2014, provisional application No. 62/048,211, filed on Sep. 9, 2014.

(51) Int. Cl.
*A61F 9/007* (2006.01)
*A61N 5/06* (2006.01)
*A61N 5/067* (2006.01)

(52) U.S. Cl.
CPC .......... *A61F 9/0079* (2013.01); *A61N 5/0613* (2013.01); *A61N 5/0624* (2013.01);
(Continued)

(58) Field of Classification Search
CPC ... A61F 9/0079; A61N 5/0613; A61N 5/0624; A61N 2005/0643; A61N 2005/0648;
(Continued)

(56) References Cited

U.S. PATENT DOCUMENTS

| 4,917,486 A | 4/1990 | Raven et al. |
| 4,930,504 A | 6/1990 | Diamantopoulos et al. |

(Continued)

FOREIGN PATENT DOCUMENTS

| CN | 2453879 Y | 10/2001 |
| EP | 2532747 | 12/2012 |

(Continued)

OTHER PUBLICATIONS

Begum et al., "Treatment with 670 nm Light Up Regulates Cytochrome C Oxidase Expression and Reduces Inflammation in an Age-Related Macular Degeneration Model," *PLoS ONE* 8(2), e57828, 2013. (11 pages).

(Continued)

*Primary Examiner* — Niketa Patel
*Assistant Examiner* — Vynn Huh
(74) *Attorney, Agent, or Firm* — Seed IP Law Group LLP

(57) ABSTRACT

An ophthalmic phototherapy device and associated treatment methods to expose an eye to selected multi-wavelengths of light to promote the healing of damaged or diseased eye tissue. The device includes a housing having an interior; an eyepiece disposed on the housing and configured and arranged for placement of an eye of the patient adjacent the eyepiece; a first light source producing a first light beam having a first therapeutic wavelength and disposed within the housing; a second light source producing a second light beam having a second therapeutic wavelength and disposed within the housing, where the second therapeutic wavelength differs from the first therapeutic wavelength by at least 25 nm.

20 Claims, 8 Drawing Sheets

(52) U.S. Cl.
CPC ............... *A61N 2005/067* (2013.01); *A61N 2005/0643* (2013.01); *A61N 2005/0648* (2013.01)

(58) Field of Classification Search
CPC ...... A61N 2005/067; A61N 2005/0635; A61N 2005/0658; A61N 2005/0664; A61N 2005/073
USPC ........................................................ 606/2–19
See application file for complete search history.

(56) References Cited

U.S. PATENT DOCUMENTS

| | | | |
|---|---|---|---|
| 4,940,323 | A | 7/1990 | Downing |
| 5,259,380 | A | 11/1993 | Mendes et al. |
| 5,290,272 | A | 3/1994 | Burstein et al. |
| 5,426,662 | A | 6/1995 | Mefford et al. |
| 5,447,527 | A | 9/1995 | Waldman |
| 5,520,679 | A | 5/1996 | Lin |
| 5,533,997 | A | 7/1996 | Ruiz |
| 5,683,436 | A | 11/1997 | Mendes et al. |
| 5,755,752 | A | 5/1998 | Segal |
| 5,766,233 | A | 6/1998 | Thiberg |
| 5,904,678 | A | 5/1999 | Pop |
| 5,964,749 | A | 10/1999 | Eckhouse et al. |
| 5,997,141 | A | 12/1999 | Heacock |
| 6,019,754 | A | 2/2000 | Kawesch |
| 6,238,424 | B1 | 5/2001 | Thiberg |
| 6,274,614 | B1 | 8/2001 | Richter et al. |
| 6,283,956 | B1 | 9/2001 | McDaniel |
| 6,287,296 | B1 | 9/2001 | Seiler et al. |
| 6,319,273 | B1 | 11/2001 | Chen et al. |
| 6,349,001 | B1 | 2/2002 | Spitzer |
| 6,350,275 | B1 | 2/2002 | Vreman et al. |
| 6,387,089 | B1 | 5/2002 | Kreindel et al. |
| 6,443,976 | B1 | 9/2002 | Flower et al. |
| 6,443,978 | B1 | 9/2002 | Zharov |
| 6,471,716 | B1 | 10/2002 | Pecukonis |
| 6,537,302 | B1 | 3/2003 | Thiberg |
| 6,537,304 | B1 | 3/2003 | Oron |
| 6,607,522 | B1 | 8/2003 | Hamblin et al. |
| 6,676,655 | B2 | 1/2004 | McDaniel |
| 6,677,366 | B2 | 1/2004 | Richter et al. |
| 6,689,124 | B1 | 2/2004 | Thiberg |
| 6,811,563 | B2 | 11/2004 | Savage, Jr. et al. |
| 6,887,260 | B1 | 5/2005 | McDaniel |
| 6,918,922 | B2 | 7/2005 | Oron |
| 7,014,639 | B2 | 3/2006 | Walneck et al. |
| 7,118,563 | B2 | 10/2006 | Weckwerth et al. |
| 7,303,578 | B2 | 12/2007 | De Taboada et al. |
| 7,309,348 | B2 | 12/2007 | Streeter et al. |
| 7,354,432 | B2 | 4/2008 | Eells et al. |
| 7,479,136 | B2 | 1/2009 | Dotson |
| 7,534,255 | B1 | 5/2009 | Streeter et al. |
| 7,695,504 | B2 | 4/2010 | Anders et al. |
| 7,744,590 | B2 | 6/2010 | Eells et al. |
| 7,914,523 | B2 | 3/2011 | Barolet et al. |
| 7,919,094 | B2 | 4/2011 | Schwaeble et al. |
| 8,025,687 | B2 | 9/2011 | Streeter et al. |
| 8,106,038 | B2 | 1/2012 | Margaron et al. |
| 8,167,921 | B2 | 5/2012 | Streeter et al. |
| 8,308,784 | B2 | 11/2012 | Streeter et al. |
| 8,471,967 | B2 | 6/2013 | Miao et al. |
| 8,508,830 | B1 | 8/2013 | Wang |
| 8,582,209 | B1 | 11/2013 | Amirparviz |
| 8,705,177 | B1 | 4/2014 | Miao |
| 9,192,780 | B2 | 11/2015 | McDaniel |
| 2002/0004673 | A1 | 1/2002 | Cho et al. |
| 2002/0087207 | A1 | 7/2002 | Cho et al. |
| 2002/0198575 | A1 | 12/2002 | Sullivan |
| 2003/0004556 | A1 | 1/2003 | McDaniel |
| 2003/0050674 | A1 | 3/2003 | Joshi |
| 2003/0093135 | A1 | 5/2003 | Denton et al. |
| 2004/0002694 | A1 | 1/2004 | Pawlowski et al. |
| 2004/0008523 | A1 | 1/2004 | Butler |
| 2004/0030370 | A1 | 2/2004 | Lytle |
| 2004/0116909 | A1 | 6/2004 | Neuberger et al. |
| 2004/0158234 | A1* | 8/2004 | Previn ................... A61F 9/008 606/6 |
| 2004/0193234 | A1 | 9/2004 | Butler |
| 2004/0215293 | A1* | 10/2004 | Eells ................... A61N 5/0613 607/89 |
| 2004/0243198 | A1 | 12/2004 | Heacock et al. |
| 2005/0055015 | A1 | 3/2005 | Buzawa |
| 2005/0149150 | A1 | 7/2005 | McDaniel |
| 2005/0159793 | A1 | 7/2005 | Streeter |
| 2005/0203592 | A1 | 9/2005 | Teichert |
| 2005/0234527 | A1 | 10/2005 | Slatkine |
| 2005/0240168 | A1 | 10/2005 | Neuberger et al. |
| 2006/0004306 | A1 | 1/2006 | Altshuler et al. |
| 2006/0184214 | A1 | 8/2006 | McDaniel |
| 2006/0235493 | A1 | 10/2006 | Dotson |
| 2007/0123844 | A1 | 5/2007 | Henry |
| 2007/0244526 | A1 | 10/2007 | Zaghetto et al. |
| 2007/0252951 | A1 | 11/2007 | Hammer et al. |
| 2008/0009839 | A1 | 1/2008 | Dotson |
| 2008/0009922 | A1 | 1/2008 | Bille |
| 2008/0234668 | A1 | 9/2008 | Linnik et al. |
| 2008/0246920 | A1* | 10/2008 | Buczek ................... A61B 90/36 351/221 |
| 2008/0269730 | A1 | 10/2008 | Dotson |
| 2008/0269849 | A1 | 10/2008 | Lewis |
| 2009/0062779 | A1 | 3/2009 | Rizoiu et al. |
| 2009/0262308 | A1* | 10/2009 | Ogawa ................... F21V 9/00 353/31 |
| 2009/0309959 | A1 | 12/2009 | Iwai et al. |
| 2010/0010592 | A1 | 1/2010 | De Taboada et al. |
| 2010/0010594 | A1 | 1/2010 | De Taboada et al. |
| 2010/0016783 | A1 | 1/2010 | Bourke, Jr. et al. |
| 2010/0079356 | A1 | 4/2010 | Hoellwarth |
| 2010/0079865 | A1 | 4/2010 | Saarikko et al. |
| 2011/0237999 | A1 | 9/2011 | Muller et al. |
| 2013/0009853 | A1 | 1/2013 | Hesselink et al. |
| 2013/0023966 | A1 | 1/2013 | Depfenhart et al. |
| 2013/0033756 | A1 | 2/2013 | Spitzer et al. |
| 2013/0053929 | A1 | 2/2013 | Colbaugh |
| 2013/0060187 | A1* | 3/2013 | Friedman ............... A61F 9/0008 604/20 |
| 2013/0069985 | A1 | 3/2013 | Wong et al. |
| 2013/0079759 | A1 | 3/2013 | Dotson et al. |
| 2013/0088413 | A1 | 4/2013 | Raffle et al. |
| 2013/0100362 | A1 | 4/2013 | Saeedi et al. |
| 2013/0103014 | A1* | 4/2013 | Gooding ................ A61B 3/102 606/6 |
| 2013/0258270 | A1 | 10/2013 | Cazalet et al. |
| 2014/0128941 | A1* | 5/2014 | Williams ................ A61N 5/06 607/88 |
| 2014/0171624 | A1 | 6/2014 | Krammer et al. |
| 2014/0194957 | A1* | 7/2014 | Rubinfeld ............. A61N 5/062 607/94 |

FOREIGN PATENT DOCUMENTS

| | | |
|---|---|---|
| JP | 2006-101940 A | 4/2006 |
| WO | 01/43825 A1 | 6/2001 |
| WO | WO2004105873 | 9/2004 |
| WO | 2005/025672 A1 | 3/2005 |
| WO | WO2008009062 | 1/2008 |
| WO | WO2012070054 | 5/2012 |
| WO | WO2012167944 | 12/2012 |
| WO | WO2013062654 | 5/2013 |
| WO | WO 2013148713 A1 * | 10/2013 ......... A61K 41/0057 |
| WO | WO 2014118571 A1 * | 8/2014 ........... A61N 5/0613 |
| WO | 2016/040534 A1 | 3/2016 |

OTHER PUBLICATIONS

Belevich et al., "Exploring the proton pump mechanism of cytochrome c oxidase in real time," *Proceedings of the National Academy of Sciences of the United States of America* 104(8):2685-2690, 2007.

(56) References Cited

OTHER PUBLICATIONS

Belevich et al., "Initiation of the proton pump of cytochrome c oxidase," *Proceedings of the National Academy of Sciences of the United States of America* 107(43):18469-18474, 2010.

Belevich et al., "Proton-coupled electron transfer drives the proton pump of cytochrome c oxidase," *Nature* 440(7085):829-832, 2006.

Brodeur, FLIP4, URL=www.spatrends.com/index, download date Mar. 1, 2005, 1 page.

Chung et al., "The Nuts and Bolts of Low-level Laser (Light) Therapy," *Annals of Biomedical Engineering* 40(2):516-533, 2012.

Damico et al., "New approaches and potential treatments for dry age-related macular degeneration," *Arquivos Brasileiros de Oftalmologia* 75(1):71-75, 2012.

Darlot et al., "Near-Infrared Light Is Neuroprotective in a Monkey Model of Parkinson Disease," *Annals of Neurology* 79(1):59-75, 2016.

De Taboada et al., "Transcranial Laser Therapy Attenuates Amyloid-β Peptide Neuropathology in Amyloid-β Protein Precursor Transgenic Mice," *Journal of Alzheimer's Disease* 23(3):521-535, 2011.

Eells et al., "Mitochondrial signal transduction in accelerated wound and retinal healing by near-infrared light therapy," *Mitochondrion* 4(5-6):559-567, 2004.

Final Office Action, dated Mar. 12, 2008, for U.S. Appl. No. 11/106,416, Dotson, "Ophthalmic Phototherapy Device and Associated Treatment Method," 8 pages.

Funk et al., "Outer Segments of Retinal Photoreceptors—A Review in the Light of Novel Findings," *Annual Research & Review in Biology* 4(16):2553-2565, 2014. (Abstract Only).

Gkotsi et al., "Recharging mitochondrial batteries in old eyes. Near infra-red increases ATP," *Experimental Eye Research* 122:50-53, 2014.

Gorbikova et al., "The proton donor for O-O bond scission by cytochrome c oxidase," *Proceedings of the National Academy of Sciences of the United States of America* 105(31):10733-10737, 2008.

Hashmi et al., "Role of Low-Level Laser Therapy in Neurorehabilitation," *PM&R* 2(12), (Supplement):S292-S305, 2010. (25 pages).

Huang et al., "Biphasic Dose Response in Low Level Light Therapy—An Update," *Dose-Response* 9(4):602-618, 2011.

Huang et al., "Biphasic Dose Response in Low Level Light Therapy," *Dose-Response* 7(4):358-383, 2009.

Huang et al., "Low-level laser therapy (810 nm) protects primary cortical neurons against excitotoxicity in vitro," *Journal of Biophotonics* 7(8):656-664, 2014.

Huang et al., "Low-level laser therapy (LLLT) reduces oxidative stress in primary cortical neurons in vitro," *J Biophotonics* 6(10):829-838, 2013.

Ivandic et al., "Low-Level Laser Therapy Improves Vision in Patients with Age-Related Macular Degeneration," *Photomedicine and Laser Surgery* 26(3):241-245, 2008.

Jasaitis et al., "Nanosecond electron tunneling between the hemes in cytochrome $bo_3$," *Proceedings of the National Academy of Sciences of the United States of America* 104(52):20811-20814, 2007.

Johnstone et al., "The potential of light therapy in Parkinson's disease," *ChronoPhysiology and Therapy* 4:1-14, 2014.

Johnstone et al., "Turning on Lights to Stop Neurodegeneration: The Potential of Near Infrared Light Therapy in Alzheimer's and Parkinson's Disease," *Frontiers in Neuroscience* 9:Article 500, 2015. (15 pages).

Kaila et al., "Prevention of leak in the proton pump of cytochrome c oxidase," *Biochimica et Biophysica Acta* 1777(7-8):890-892, 2008.

Karu et al., "Exact Action Spectra for Cellular Responses Relevant to Phototherapy," *Photomedicine and Laser Surgery* 23(4):355-361, 2005.

Karu, "Mechanisms of Low-Power Laser Light Action on Cellular Level," *Proceedings of SPIE* 4159, 2000. (17 pages).

Laakso et al. (ed.), *Proceedings of the 9th World Association for Laser Therapy Congress,* Foreword and Index, Gold Coast, Australia, Sep. 28-30, 2012, 6 pages.

Lane, "Power Games," *Nature* 443(7114):901-903, 2006.

Light Bioscience, "Gentlewaves LED Photomodulation Device," downloaded from http://www.lightbioscience.com/led_device.html on Mar. 1, 2005, 1 page.

Lubart et al., "Low Energy Laser Irradiation Promotes Cellular Redox Activity," *Photomedicine and Laser Surgery* 23(1):3-9, 2005. (15 pages).

LumiThera, "Photobiomodulation for eye diseases," Selected Abstracts, Aug. 21, 2013. (24 pages).

Masha et al., "Low-Intensity Laser Irradiation at 660 nm Stimulates Transcription of Genes Involved in the Electron Transport Chain," *Photomedicine and Laser Surgery* 31(2):47-53, 2013.

Merry et al., "Treatment of dry Age-related Macular Degeneration with Photobiomodulation," *Annual Meeting of the Association for Research in Vision and Ophthalmology,* Fort Lauderdale, FL, USA, May 6-9, 2012, 12 pages.

Moro et al., "Photobiomodulation preserves behaviour and midbrain dopaminergic cells from MPTP toxicity: evidence from two mouse strains," *BMC Neuroscience* 14:Article 40, 2013. (9 pages).

Office Action, dated Apr. 3, 2007, for U.S. Appl. No. 11/106,416, Dotson, "Ophthalmic Phototherapy Device and Associated Treatment Method," 10 pages.

Office Action, dated Feb. 25, 2008, for U.S. Appl. No. 11/858,351, Dotson, "Ophthalmic Phototherapy Treatment Method," 12 pages.

Office Action, dated Jan. 14, 2015, for U.S. Appl. No. 13/679,557, Dotson et al., "Ophthalmic Phototherapy Device and Associated Treatment Method," 29 pages.

Office Action, dated May 23, 2012, for U.S. Appl. No. 12/172,697, Dotson, "Ophthalmic Phototherapy Device and Associated Treatment Method," 31 pages.

Oron et al., "Low-level laser therapy applied transcranially to mice following traumatic brain injury significantly reduces long-term neurological deficits," *Journal of Neurotrauma* 24(4):651-656, 2007. (Abstract Only).

Purushothuman et al., "Photobiomodulation with near infrared light mitigates Alzheimer's disease-related pathology in cerebral cortex—evidence from two transgenic mouse models," *Alzheimer's Research & Therapy* 6(2), 2014. (13 pages).

Riverside Facial Plastic Surgery and Sinus Center, Gentlewaves LED Photomodulation Fact Sheet, URL=http://www.riversideface.com/pages/gentlewaves.html, download date Mar. 9, 2015. (4 pages).

Robotic LED Skin Rejuvenation, FLIP4, URL=www.medspafinancing.com/new.html, download date Mar. 1, 2005, 1 page.

Rodríguez-Santana et al., "Laser Photobiomodulation as a Potential Multi-Hallmark Therapy for Age-Related Macular Degeneration," *Photomedicine and Laser Surgery* 31(9):409-410, 2013.

Rojas et al., "Low-level light therapy of the eye and brain," *Eye and Brain* 3:49-67, 2011.

Sharma et al., "Dose Response Effects of 810 nm Laser Light on Mouse Primary Cortical Neurons," *Lasers in Surgery and Medicine* 43(8):851-859, 2011. (16 pages).

Siletsky et al., "Time-resolved single-turnover of $ba_3$ oxidase from *Thermus thermophilus,*" *Biochimica et Biophysica Acta* 1767(12):1383-1392, 2007.

Sommer et al., "Biostimulatory Windows in Low-Intensity Laser Activation: Lasers, Scanners, and NASA's Light-Emitting Diode Array System," *Journal of Clinical Laser Medicine & Surgery* 19(1):29-33, 2001.

Tang et al., "Low-Intensity Far-Red Light Inhibits Early Lesions That Contribute to Diabetic Retinopathy: In Vivo and In Vitro," *Investigative Ophthalmology & Visual Science* 54(5):3681-3690, 2013.

Tarita-Nistor et al., "Fixation Characteristics of Patients with Macular Degeneration Recorded with the MP-1 Microperimeter," *Retina* 28(1):125-133, 2008. (Abstract Only).

Tosk, "FDA Clears GentleWaves: The First and Only Light Emitting Diode Device for the Treatment of Periorbital Wrinkles and Rhytids," URL=http://www.drmcdaniel.com/fda-clears-gentlewaves, download date Mar. 9, 2015, 2 pages.

Tuchin, *Tissue Optics: Light Scattering Methods and Instruments for Medical Diagnosis,* The International Society for Optical Engineering, Bellingham, WA, USA, 2000, pp. 1-11.

(56) References Cited

OTHER PUBLICATIONS

Xuan et al., "Transcranial Low-Level Laser Therapy Improves Neurological Performance in Traumatic Brain Injury in Mice: Effect of Treatment Repetition Regimen," *PLoS ONE* 8(1), e53454, 2013. (9 pages).
Barnstable et al., "Neuroprotective and antiangiogenic actions of PEDF in the eye: molecular targets and therapeutic potential," *Progress in Retinal and Eye Research* 23:561-577, 2004.
Glaser et al., "Retinal Pigment Epithelial Cells Release Inhibitors of Neovascularization," *Ophthalmology* 94:780-784, 1987.
Grossman et al., "780 nm Low Power Diode Laser Irradiation Stimulates Proliferation of Keratinocyte Cultures: Involvement of Reactive Oxygen Species," *Lasers in Surgery and Medicine* 22:212-218, 1998.
Hamblin et al., "Mechanisms of Low Light Therapy," *Proc. of SPIE* 6140(614001): 2006, 12 pages.
International Organization for Standardization, "Opthalmic instruments—Fundamental requirements and test methods—Part 2: Light hazard protection," ISO 15004-2:2007(E) first edition, 2007, 42 pages.
Karu et al., "Cell Attachment to Extracellular Matrices in Modulated by Pulsed Radiation at 820 nm and Chemicals that Modify the Activity of Enzymes in the Plasma Membrane," *Lasers in Surgery and Medicine* 29:274-281, 2001.
Karu et al., "Cellular Effects of Low Power Laser Therapy Can be Mediated by Nitric Oxide," *Lasers in Surgery and Medicine* 36:307-314, 2005.
Karu et al., "Irradiation with He—Ne laser increases ATP level in cells cultivated in vitro," *Journal of Photochemistry and Photobiology B: Biology* 27:219-223, 1995.
Kiire et al., "Subthreshold Micropulse Laser Therapy for Retinal Disorders," *Retina Today*, 2011, pp. 67-70.
Lim et al., "Probe pressure effects on human skin diffuse reflectance and fluorescence spectroscopy measurements," *Journal of Biomedical Optics* 16(1):011012, 2011, 9 pages.
Lisman et al., "Two Light-Induced Processes in the Photoreceptor Cells of Limulus Ventral Eye," *The Journal of General Physiology* 58:544-561, 1971.
Miller et al., "The Role of Retinal Pigment Epithelium on the Involution of Subretinal Neovascularization," *Invest Ophthalmol Vis Sci.* 27(11):1644-1652, 1986.
Murphy et al., "Toward the discrimination of early melanoma from common and dysplastic nevus using fiber optic diffuse reflectance spectroscopy," *Journal of Biomedical Optics* 10(6):064020, 2005, 9 pages.
Ogata et al., "Upregulation of Pigment Epithelium-Derived Factor after Laser Photocoagulation," *American Journal of Ophthalmology* 132(3):427-429.
"Product Development," LumiThera, archived Aug. 20, 2014, URL= https://web.archive.org/web/20140820101900/https://www.lumithera.com:80/products/, download date Mar. 5, 2018. (2 pages).
Tang et al., "Predicting complications with pretreatment testing in infantile haemangioma treated with oral propranolol," *British Journal of Ophthalmology* 100(7):902-906, 2016.
Tata et al., "Laser therapy: A review of its mechanism of action and potential medical applications," *Laser Photonics Rev.* 5(1):1-12, 2011.
van Breugal et al., "Power Density and Exposure Time of He—Ne Laser Irradiation Are More Important Than Total Energy Dose in Photo-Biomodulation of Human Fibroblasts In Vitro," *Lasers in Surgery and Medicine* 12(1):528-537, 1992.
Wells et al., "Biophysical mechanisms responsible for pulsed low-level laser excitation of neural tissue," *Proc of SPIE* 6084:60840X-1-60840X-7, 2006, 7 pages.
Wong-Riley et al., "Photobiomodulation Directly Benefits Primary Neurons Functionally Inactivated by Toxins," *The Journal of Biological Chemistry* 280(6):4761-4771, 2005.

\* cited by examiner

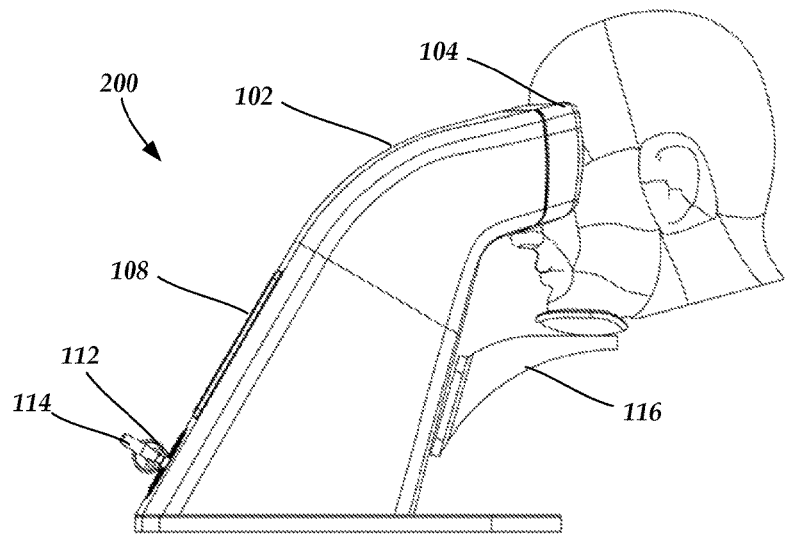
FIG. 2
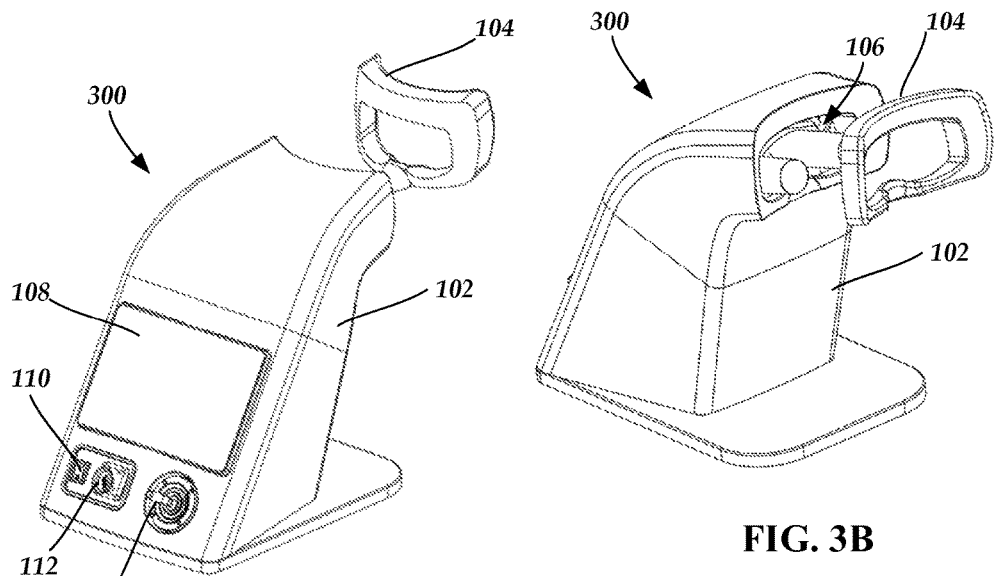
FIG. 3A
FIG. 3B

DEVICES AND METHODS FOR NON-INVASIVE MULTI-WAVELENGTH PHOTOBIOMODULATION FOR OCULAR TREATMENTS

CROSS-REFERENCE TO RELATED APPLICATIONS

This U.S. non-provisional patent application, which was filed on Sep. 9, 2015, claims the benefit of U.S. Provisional Patent Application Nos. 62/048,182, 62/048,187, and 62/048,211, each of which was filed on Sep. 9, 2014, and claims priority to PCT Patent Application No. PCT/US15/49261, which was also filed on Sep. 9, 2015 and claims the benefit of U.S. Provisional Patent Application Nos. 62/048,182, 62/048,187, and 62/048,211. U.S. Provisional Patent Application Nos. 62/048,182, 62/048,187, and 62/048,211 and PCT Patent Application No. PCT/US15/49261 are incorporated herein by reference in their entirety.

BACKGROUND OF THE DISCLOSURE

Technical Field

The present disclosure relates to an ophthalmic phototherapy device and an associated treatment methods using non-invasive light therapy. In addition, the present disclosure is related to devices and methods for exposing an eye to selected wavelengths of light to promote the healing of damaged or diseased eye tissue.

Description of the Related Art

Light can act on different mechanisms within cellular tissue to stimulate or suppress biological activity in a process commonly referred to as photobiomodulation ("PBM"). PBM requires the use of light with a suitable intensity, energy, and wavelengths, without significantly causing damage to the cells. The combination of characteristics suitable for photobiomodulation applications are distinct from those of light used in other applications.

There are many disorders including trauma or diseases that can afflict the eye. Ocular disease can include, for example, glaucoma, age-related macular degeneration, diabetic retinopathy, retinitis pigmentosa, CRS, NAION, Leber's disease, uveitis, and the like. Other disorders can include physical trauma (e.g., cataract or lens surgery) or other sources of ocular injury, damage or degeneration. Ocular degeneration can include the process of cell destruction resulting from a primary destructive event such as ocular trauma or surgery, as well as from secondary, delayed and progressive destructive mechanisms that are invoked by cells due to the occurrence of a primary destructive or disease event.

It is desirable to develop methods and devices for treatment of these ocular diseases, disorders, or degeneration. In particular, it is desirable to develop methods and devices for treatment that may be less invasive or have fewer side effects than surgery or pharmacological treatments or which can be used in conjunction with surgery or pharmacological treatments to aid in healing or treatment.

SUMMARY OF THE DISCLOSURE

In at least some embodiments, an apparatus adapted to provide light therapy to a subject experiencing symptoms associated with one or more ocular disorders or disease or a subject who has been diagnosed with one or more ocular disorders or disease through the eye of the subject either with the open or closed eyelid, sclera or any angle approach that provides for access to the target tissues. The apparatus can include a controller that can operate in a standalone, independent manner, or in response to a signal from a remote control. The controller can activate one or more light sources adapted to delivery light to the subject's ocular tissue.

In at least some embodiments, the apparatuses and methods described herein can be used to treat, or otherwise improve the resultant effects of ocular conditions, such as acute or chronic ocular diseases, or the symptoms associated with such ocular conditions. In at least some embodiments, the apparatus and methods described herein can be used to treat or otherwise improve the symptoms or effects associated with ocular degenerating diseases, such as blurred or loss of vision, visual acuity impairment, inflammation, and deterioration in contrast sensitivity. In accordance with several embodiments, the apparatuses and methods described herein are used to treat, or otherwise address subjects having, or experiencing symptoms of acute or chronic ocular syndromes (e.g., glaucoma, age-related macular degeneration (AMD), diabetic retinopathy, retinitis pigmentosa, central serous retinopathy (CRS), non-arteritic anterior ischemic optic neuropathy (NAION), Leber's disease, ocular surgery, uveitis, hypertensive retinopathy, or any process that interferes with function via vascular or neurological mechanism, and optic neuritis. The apparatuses and methods described herein can also be used to treat, or otherwise address subjects having acute and chronic ocular eyelid disease including bleparitis, periorbital wrinkles, seborrhea and other eyelid skin conditions i.e. psoriasis, eczema, etc. The apparatuses and methods described herein can also be used to treat, or otherwise address subjects having acute and chronic ocular conjunctiva and corneal disease including any acute injuries such as exposure keratitis or UV keratitis, dry eyes, viral infections, bacterial infections, corneal abrasions, corneal oedema, surgical incisions, perforating injuries, episcleritis and scleritis. The apparatuses and methods described herein can also be used to treat, or otherwise address subjects having acute and chronic anterior chamber and vitreous disease including iritis, vitritis, endophthalmitis (bacterial and sterile).

Categories are generally determined based on the area affected or on the etiology and it should be appreciated that some disorders, diseases, or conditions can overlap between two or more categories.

One embodiment is a self-standing device for delivery of light therapy to ocular tissue of an eye of a patient. The device includes a housing having an interior; an eyepiece disposed on the housing and configured and arranged for placement of an eye of the patient adjacent the eyepiece; a first light source producing a first light beam having a first therapeutic wavelength and disposed within the housing; a second light source producing a second light beam having a second therapeutic wavelength and disposed within the housing where the second therapeutic wavelength differs from the first therapeutic wavelength by at least 25 nm; and an aperture disposed within the housing. The device is configured and arranged to direct the first and second light beams through the aperture and through the eyepiece to provide light therapy to the eye of the patient.

Another embodiment is a self-standing device for delivery of light therapy to ocular tissue of an eye of a patient. The device includes a housing having an interior; an eyepiece disposed on the housing and configured and arranged for placement of an eye of the patient adjacent the eyepiece; a first light source producing a first light beam having a first therapeutic wavelength and disposed within the housing; a second light source producing a second light beam having a second therapeutic wavelength and disposed within the housing where the second therapeutic wavelength differs from the first therapeutic wavelength by at least 25 nm; and a reflective filter disposed within the housing and configured and arranged to substantially pass light having the first therapeutic wavelength and substantially reflect light having the second therapeutic wavelength. The device is configured and arranged to direct the first and second light beams to the reflective filter and then through the eyepiece to provide light therapy to the eye of the patient.

A further embodiment is a method of providing light therapy to ocular tissue of a patient using any of the apparatuses or devices described above. The method includes placing at least one eye of the patient at the eyepiece of the device; and directing light of at least one of the first therapeutic wavelength or the second therapeutic wavelength from device to the at least one eye of the patient to produce a therapeutic effect.

BRIEF DESCRIPTION OF THE DRAWINGS

These and other aspects of the present disclosure will be best understood in conjunction with the following drawings, which exemplify certain aspects of the various embodiments.

FIG. 2 is a side view of one embodiment of a second embodiment of an opthalmic phototherapy device with a chin rest, according to the present disclosure.

FIG. 3A is a perspective back view of a third embodiment of an opthalmic phototherapy device with a removable patient interface surface, according to the present disclosure.

FIG. 3B is a perspective side view of the opthalmic phototherapy device of FIG. 3A, according to the present disclosure.

DETAILED DESCRIPTION

Figure 1A:
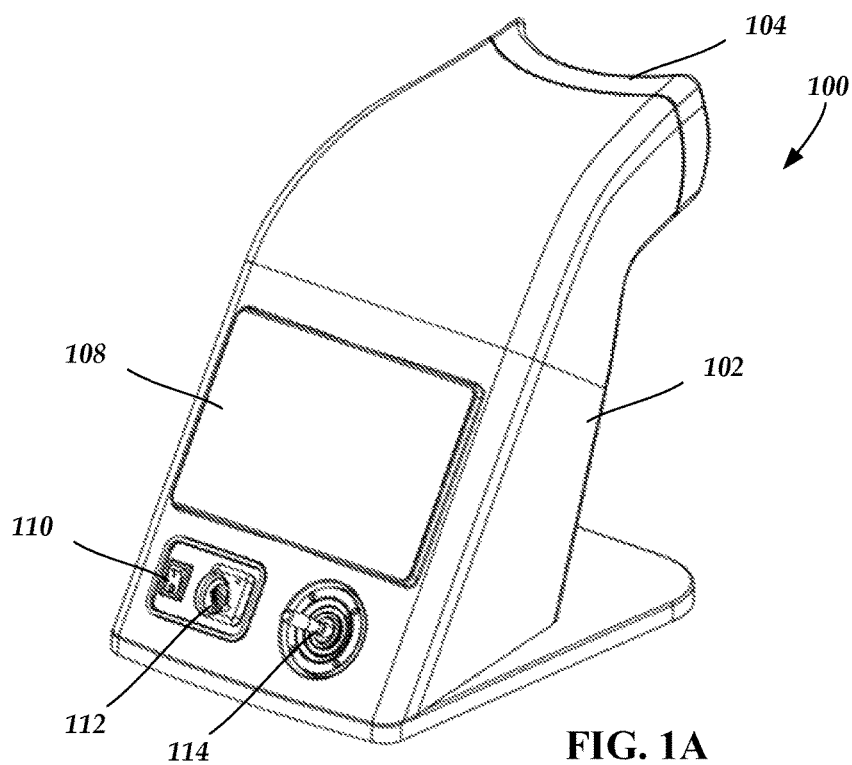
FIG. 1A is a perspective back view of one embodiment of an opthalmic phototherapy device, according to the present disclosure.
Figure 1B:
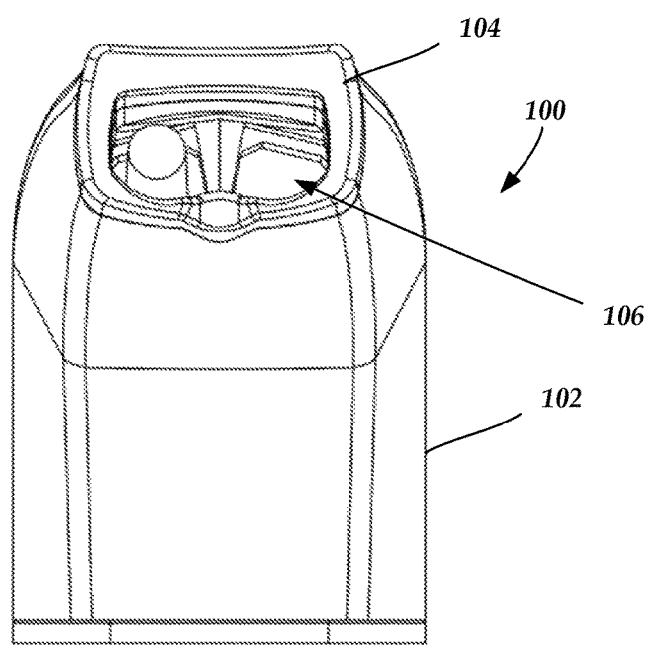
FIG. 1B is a front view of the opthalmic phototherapy device of FIG. 1A, according to the present disclosure.
Figure 1C:
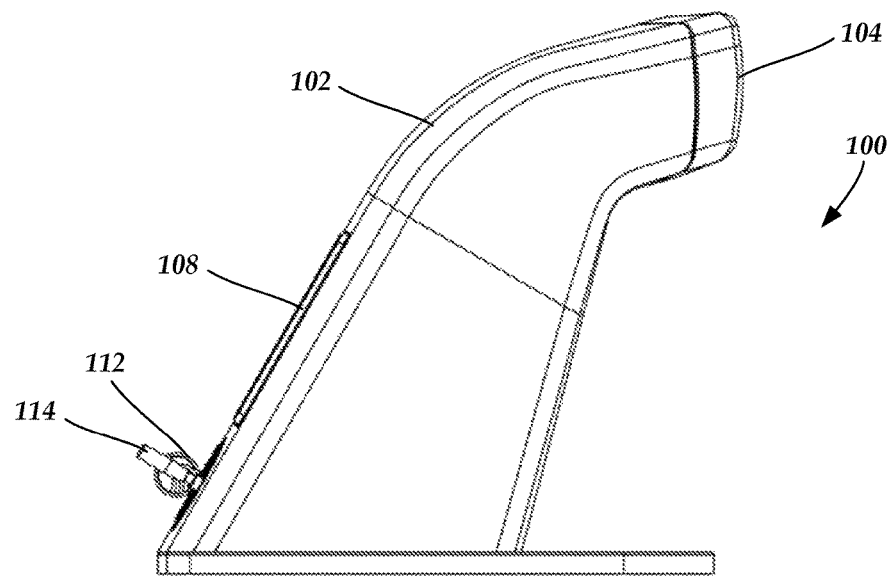
FIG. 1C is a side view of the opthalmic phototherapy device of FIG. 1A, according to the present disclosure.
Figure 1D:
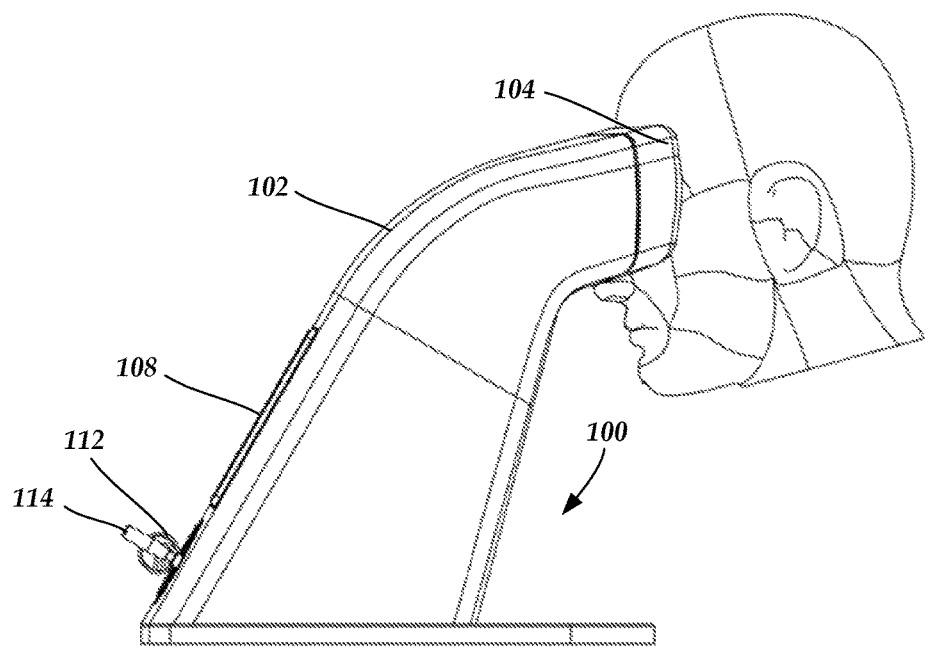
FIG. 1D is a side view of the opthalmic phototherapy device of FIG. 1A with a patient, according to the present disclosure.

The multi-wavelength phototherapy devices, systems and methods, which are described in further detail herein, are based upon the discovery that certain cellular responses, including cellular responses within a damaged and/or diseased tissue, can be promoted through the coordinated and targeted delivery to a cell of light having two distinct wavelengths, wherein a first dose of light having a first wavelength (or range of wavelengths) can stimulate a first intracellular activity and a second dose of light having a second wavelength (or range of wavelengths) can stimulate a second intracellular activity. Moreover, certain therapeutic benefits can be achieved in a patient afflicted with a damaged and/or diseased tissue by promoting a desired cellular response that contributes to the healing of a damaged tissue and/or reversal or slowing of disease progression in a diseased tissue.

Photobiomodulation ("PBM") is a non-invasive form of low level light therapy ("LLLT") that involves the therapeutic administration of light energy to a subject (e.g., a human or animal) at lower irradiances than those used for cutting, cauterizing, or ablating biological tissue, resulting in desirable photobiomodulatory effects while leaving tissue undamaged. In non-invasive phototherapy, it is desirable to apply an efficacious amount of light energy to the internal tissue to be treated using light sources positioned outside the body. (See, e.g., U.S. Pat. Nos. 6,537,304 and 6,918,922, both of which are incorporated in their entireties by reference herein.)

Therapeutic benefits can be achieved for a patient afflicted with damaged and/or diseased tissue by promoting one or more cellular responses within a cell of a damaged and/or diseased tissue, which cellular responses can be promoted through the coordinated and targeted delivery of two or more doses of light, wherein a first dose of light has a first wavelength or range of wavelengths, which can stimulate a first intracellular activity, and a second dose of light has a second wavelength or range of wavelengths, which can stimulate a second intracellular activity, wherein the coordinated stimulation of the first and second intracellular activities promotes a desired cellular response thereby facilitating healing of the damaged tissue and/or reversing or slowing disease progression in the diseased tissue.

The present disclosure relates, at least in part, to ophthalmic multi-wavelength phototherapy devices and associated treatment methods. A device and method for exposing an eye to selected wavelengths of light that can promote the healing of damaged or diseased eye tissue. For example, a self-standing apparatus or device for use in an office or elsewhere can deliver a therapeutic, independently controlled, multi-wavelength combination of low level light to ophthalmologic tissue. Treatment may include, for example targeting of damaged or diseased tissue with an ophthalmologic device capable of delivering multi-wavelength phototherapy therapeutics alone. Device and sensors or other imaging modalities may be used to establish the optimal ocular spatial and tissue parameters to provide an efficacious treatment to the eye. In at least some embodiments, the multi-wavelength device is used in combination with other pharmaceuticals or devices to enhance or personalize phototherapy treatment to ocular tissues.

The coordinated, independent use of selected wavelengths and the application of selected combinations of multi-wavelength PBM can create highly targeted, beneficial cellular responses. In at least some embodiments, a therapeutic approach to treat ocular disease or disorders can use the combination of two or more wavelengths alone or the use of one or more wavelengths in combination with a medical device, biologic or pharmaceutical to provide a desired therapeutic utility.

The use of individual wavelengths, such as red light (640-700 nm) or near infrared (NIR) light (800-900 nm), can each individually stimulate mitochondrial cytochrome C oxidase (CCO) enzyme activity as found in both in vitro and in vivo studies. It is found, however, that the individual wavelengths target distinct copper sites (e.g., CuA and CuB) within the multi-subunits of CCO and produce distinct biological responses. Thus, the coordinated use of both wavelengths in combination to target CuA and CuB) and to sequentially enhance both electron transfer and oxygen binding on the CCO enzyme can, at least in some embodiments, improve overall therapeutic CCO efficacy. The efficiency of CCO activity, restoration of mitochondrial membrane potential (MMP) and improvements in adenosine triphosphate (ATP) synthesis may all be intimately linked. This multi-wavelength approach may be used, at least in some embodiments, to restore MMP or to increase ATP formation (e.g. in a disease or disorder wherein the absence of or limited availability of oxygen is seen). In an example, when blood flow is restricted, the use of one wavelength (in the range of 640-700 nm on CuB) may initially displace inhibitors, such as Nitric Oxide (NO), from the oxygen binding site. NO is a potent vasodilator and local NO release from mitochondria may improve local blood flow, increasing $O_2$ and nutrients into the diseased tissue area. In addition, stimulation with light having a wavelength in the range of 640-700 nm may preferentially increase $O_2$ binding affinity to the active site to stimulate electron transport and aerobic generated ATP. In other instances, where electron chain transfer of electrons from cytochrome C to CCO is dysfunctional and a more viable pathway for addressing ATP generation, may target CuA treatment with NIR at, for example, 810 nm (or in the range of 800 to 900 nm) may provide for photo-mediated, transfer of electrons from cytochrome C and improved efficiency of electron flow with restoration of MMP. In some embodiments, the use of both wavelengths concurrently or in some sequence with pre-defined optical parameters (e.g., duration, frequency, continuous or pulsed, fluence level) can provide a treatment to restore mitochondrial function. Utilization of independently controlled, multi-wavelength light therapy may allow for enhancement or optimization of therapeutic effects and can be monitored or tailored to the disorder or disease state.

The use of multi-wavelength phototherapy may be tailored to effect important intracellular mediators. ATP, guanosine triphosphate (GTP), NO, reactive oxidative species (ROS) are all used by cells as the active substrates for signal transduction, which is the process known to transmit intracellular stimuli, which in turn regulates numerous cellular pathways and subsequent cellular activity. Control of cellular pathways by specific second messengers can provide a key regulator mechanism of cell activity. Protein kinases represent a major class of enzymes that lead to the phosphorylation of protein targets. ATP is the active substrate for protein kinases and used to transfer the high energy phosphorous bond to the target proteins. Protein activity can be increased or decreased by one or more phosphorylation sites. Therefore, enzyme or cellular pathway activity can be greatly controlled by the availability of ATP and ATP levels in the cell, either through inhibition or activation of specific protein targets by protein kinases. The use of multiple wavelengths of light can facilitate one or more objections such as, for example, regulate signal transduction, mediate protein kinase activity, improve cellular performance, or restore cellular function in damage or diseased tissue. The combined benefits of photons from one or more wavelengths can facilitate regulating second messengers affecting a specific pathway. For example, a light therapy could include the use of NO, ROS or ATP monitoring in the role of combination phototherapy to establish characteristics suitable for photobiomodulation applications.

Separately, the use of multiple wavelengths of light can be utilized to regulate and control cellular gene expression and restore cellular function in damage or diseased tissue. Gene expression patterns are used by cells to coordinate and regulate numerous pathways that influence subsequent cellular activity. PBM therapy (670 nm) is implicated in changing the gene expression pattern for multiple genes involved in cellular metabolism. Up regulation of several genes involved in electron chain transport, energy metabolism and oxidative phosphorylation is seen, thus rejuvenating the cells metabolic capacity and stimulating the increase in ATP production, which drives other pleiotropic processes, all leading to long-term improvement or normalization of cellular functions. Phototherapy may affect NFkβ, a major cellular regulator of inflammatory pathways and gene expression. The combined benefits of photons from one or more wavelengths can target and regulate gene expression of specific pathways. Gene expression mapping in multi-wavelength phototherapy can be used to identify characteristics suitable for photobiomodulation applications.

In at least some embodiments, the use of phototherapy in combination with gene therapy can stimulate, enhance or control the regulation and expression of novel genes incorporated into the nucleus through viral vectors or other gene therapy techniques. This is distinct from using light-activated gene products and utilizes selected wavelengths to naturally stimulate cellular gene expression profiles for newly implanted gene therapy. In at least some embodiments, the use of gene therapy can facilitate the regeneration of retinal tissue or to provide for gene therapy in the mitochondrial genetic ocular disorders, such as Leber's hereditary optic neuropathy or AMD. In those cases, gene therapy in combination with photobiomodulation (PBM) to stimulate specific mitochondrial electron transport protein expression may provide a better or optimized therapeutic combination approach.

Separately, RNA and protein expression patterns are used by cells to effectively regulate numerous pathways and subsequent cellular activity. Multiple wavelengths of light can be used to indirectly regulate and improve RNA and protein expression and restore cellular function in damage or diseased tissue. Protein mapping can be used in combination with phototherapy to identify characteristics suitable for photobiomodulation applications. AMD is considered a chronic inflammatory disease where protein deposits further propagate the inflammatory state and disease progression. Therefore, the use of multi-wavelength PBM can deliver a combination therapeutic. In RPE cell studies, the use of 590 nm light has been shown to inhibit VEGF expression and thus the use of 590 nm PBM (or another wavelength in the range of 500 to 650 nm) can be useful in the treatment of wet AMD subtype to suppress VEGF protein expression locally in ocular tissue. VEGF antibody treatment (Lucentis®) is a currently approved pharmaceutical treatment for wet AMD.

Separately, the use of 810 nm PBM (or another wavelength in the range of 800 to 900 nm) can improve mitochondrial function, reduce inflammatory markers, or prevent β-amyloid deposits in age-related Alzheimer's mice (or any combination of these effects). Further, the use of 670 nm PBM (or another wavelength in the range of 600 to 750 nm) can reduce inflammatory markers like complement C3 expression and deposition in AMD mouse models but does not affect b-amyloid deposition. Both deposition of lipofusion and β-amyloid have been implicated in the etiology of the diseased eyes in AMD patients. The combinations of multi-wavelengths PBM can be used alone or used with one or more drugs, such as, for example, one or more of an anti-VEGF MoaB, (e.g. Lucentis®, Avastin®) an anti-inflammatory drug (e.g. non-steroidal, anti-inflammatory agents, anti-complement agent (e.g. Properidin, C3, MASP-2, C5 inhibitors), antioxidants or vitamin supplements (e.g., AREDS supplements (Lipotriad Visonary™, Viteyes 2®, ICaps®, and PreserVision®, contain similar constituents but either in different proportions, or with additional ingredients,) or visual cycle disruptor (e.g. isomerase inhibitors (ACU-4429).

In at least some embodiments, the targeted use of phototherapy to improve mitochondrial function via increased CCO activity, restoration of MMP and regulation of ATP synthesis may be achieved by the use of multiple wavelengths of light to create the appropriate local cellular response to damage or disease. Localized cellular conditions in trauma and disease may differ across discrete tissue or organ areas and are under dynamic local regulation. For example, phototherapy of local CCO activity can lead to release of inhibitory NO from the $O_2$ binding site. NO is a powerful vasodilator and signal transducer which can regulate the local blood flow to targeted tissue. This may be useful in reversing local ischemia or restricted blood flow to damaged or diseased tissue. In at least some embodiments, a treatment can include the discrete targeting of phototherapy to tissues such as within the retina and associated surrounding ocular tissue types. As an example, it may be most beneficial to treat discrete local optic nerve ischemia as seen in non-arteric ischemic optic neuropathy (NAION). In another example, it may be most beneficial to target anatomical islands of cellular deposits that may be a nidus for inflammation, ischemia or disease in dry AMD. In early stage AMD, discrete cellular deposits of lipofusion can be identified on the retina by standard imaging techniques (OCT, fluorescence imaging). In such an example, the use of imaging modalities such as OCT or fluorescence may be used to target the multi-wavelength phototherapy to slow the disease, stop or reverse the deposition of proteins such as lipofusion or β-amyloid and reduce, slow or stop the progression of the disease. These targeted phototherapy applications provide a disease-modifying approach to chronic ocular disease. An instrument can produce phototherapy alone or in combination with OCT or some other imaging devices (e.g., PET, MRI, Ultra-sound, Doppler, Fluorescence, Femtosensors, etc.) as an approach to identify discrete areas of interest and target cell or tissue boundaries with a combination of wavelengths to enhance, optimize, or personalize patient treatment. In another such example, imaging modalities, such as femtosensors to monitor local retinal $O_2$ levels, may be used to identify AMD patients with local hypoxia and to combine with phototherapy to improve treatments and to monitor increased $O_2$ levels to restore mitochondrial retinal function. In at least some embodiments, the selection of wavelength and doses and treatment parameters may vary depending on the underlying disease or disorder. The independent targeting of multiple wavelengths of light can facilitate one or more of local phototherapy, individualized patient phototherapy, restored cellular performance, or to slow or stop ocular disease propagation. These approaches can be performed alone, in combination with existing diagnostic devices or as instruments combining phototherapy and diagnostic modalities.

In at least some embodiments, phototherapy includes selection of wavelengths and dosing parameters. Distinct wavelengths have individual tissue absorption properties, which impact the depth of penetration and the appropriate dose for clinical efficacy. A device can include a component, such as a camera or other sensor, that can use used to capture patient orbital features, including depth, size, skin color, or distances. This allows for setting of the dose for each wavelength separately or in combination at preset values to enhance or optimize treatment parameters. In at least some embodiments, the sensor may be used to aid in the dose selection through the open or closed eyelid, taking into account, for example, tissue color or thickness.

In at least some instances, there is some amount of intervening tissue between the light source and the target tissue. In at last some embodiments, a wavelength of light can be selected at which the absorption by intervening tissue is below a damaging level. Such embodiments may also include setting the power output of the light source at low, yet efficacious, irradiances (for example, between approximately 100 $\mu W/cm^2$ to approximately 10 $W/cm^2$) at the target tissue site, or setting the temporal profile of the light applied to the tissue (e.g., temporal pulse widths, temporal pulse shapes, duty cycles, pulse frequencies) or time periods of application of the light energy at hundreds of microseconds to minutes to achieve an efficacious energy density at the target tissue site being treated. Other parameters can also be varied in the use of phototherapy. These other parameters contribute to the light energy that is actually delivered to the treated tissue and may affect the efficacy of phototherapy.

In at least some embodiments, the target area of the subject's tissue includes the area of injury, for example, to the optic nerve and surrounding ocular tissue. In some embodiments, the target area includes portions of the eye.

In at least some embodiments, the devices and methods of phototherapy described herein are used to treat ocular disorders. As used herein, ocular disorder can refer to at least one characteristic or experiencing symptoms of ocular syndromes (e.g., glaucoma, age-related macular degeneration, diabetic retinopathy, retinitis pigmentosa, CRS, NAION, Leber's disease, ocular surgery, uveitis, or the like, and not limited to and including further indications as described throughout this application).

In at least some embodiments, the devices and methods of phototherapy described herein are used to treat physical trauma (e.g., cataract or lens surgery) or other sources of ocular inflammation or degeneration or aid in rehabilitation of the ocular degenerative effects caused by the physical trauma. Ocular degeneration can include, for example, the process of cell destruction resulting from primary destructive events such as ocular trauma or surgery, as well as from secondary, delayed and progressive destructive mechanisms that are invoked by cells due to the occurrence of the primary destructive or disease event. Primary destructive events can include disease processes or physical injury or insult, including surgery, but also include other diseases and conditions such as glaucoma, age-related macular degeneration, diabetic retinopathy, retinitis pigmentosa, CRS, NAION, Leber's disease, ocular surgery, uveitis, cerebral ischemia including focal optic nerve ischemia, and physical trauma such as crush or compression injury to ocular tissues, including a crush or compression injury of the optic nerves or retina, or any acute injury or insult producing ocular degeneration. Secondary destructive mechanisms can include any mechanism that leads to the generation and release of neurotoxic molecules, including but not limited to, apoptosis, depletion of cellular energy stores because of changes in mitochondrial membrane permeability, release or failure in the reuptake of excessive glutamate, free radical damage, reperfusion injury, deposition of insoluble proteins including lipofusin and β-amyloid and activity of complement, cytokines and inflammatory conditions. Both primary and secondary mechanisms contribute to forming a "zone of danger" for ocular tissue, where the tissue in the zone have at least temporarily survived the primary destructive event, but are at risk of dying due to processes having delayed effect.

In at least some embodiments, the devices and methods described herein are used to provide cytoprotection. Cytoprotection can include a therapeutic strategy for slowing or preventing the otherwise irreversible loss of ocular tissue due to degeneration after a primary destructive event, whether the tissue degeneration loss is due to disease mechanisms associated with the primary destructive event or secondary destructive mechanisms.

In at least some embodiments, the devices and methods described herein are used to improve ocular function, to provide ocular enhancement, to prevent or slow the progression of loss of ocular function, or to regain previously lost ocular function, or any combination thereof. Ocular function can include both visual acuity function and contrast sensitivity function.

Diseases or conditions affecting ocular function include, but are not limited to, primary destructive events, disease processes or physical injury or insult, including age-related macular degeneration and other diseases and conditions such as glaucoma, stroke, diabetic retinopathy, retinitis pigmentosa, CRS, NAION, Leber's disease, ocular surgery, uveitis, cerebral ischemia including focal optic nerve ischemia, and physical trauma such as crush or compression injury to ocular tissues, including a crush or compression injury of the optic nerves or retina, or any acute injury or insult producing ocular degeneration.

As used herein, the terms "therapeutic regimen" and "treatment regimen" refer to a protocol and associated procedures used to provide a therapeutic treatment that includes one or more periods during which light is irradiated to one or more ocular target regions. As used herein, the terms "target," "target area," and "target region" refer to a particular ocular area, region, location, structure, population, or projection (e.g., within the retina or optic nerve) to be irradiated by light in association with the treatment of a particular type of ocular condition, disease, disorder, or injury. In at least some embodiments, the irradiated portion of the eye can be the entire eye. In other embodiments, the irradiated portion of the eye is a targeted region of the eye, such as the retinal region, the macula, or the cornea.

In at least some embodiments, the methods and devices described herein can be used to promote the proliferation, migration and regenerative cellular properties of endogenous progenitor retinal stem cells for use in retinal or ocular diseases. Stem cells have the capacity to both self-renew and generate postmitotic cells. The retinal pigment epithelium (RPE) is a monolayer of cells underlying and supporting the neural retina. It begins as a plastic tissue, capable, in some species, of generating lens and retina, but differentiates early in development and remains normally nonproliferative throughout life. However, subpopulations of adult human RPE cells can be activated in vitro to a self-renewing cell, the retinal pigment epithelial stem cell (RPESC) that loses RPE markers, proliferates extensively, and can redifferentiate into stable cobblestone RPE monolayers. Clonal studies demonstrate that RPESCs are multipotent and in defined conditions can generate both neural and mesenchymal progeny. This plasticity may explain human pathologies in which mesenchymal fates are seen in the eye, for example in proliferative vitreoretinopathy (PVR) and phthisis bulbi. The RPESC as an accessible, human CNS-derived multipotent stem cell, useful for the study of fate choice, replacement therapy, and disease modeling.

In at least some embodiments, the methods and devices described herein can be used to promote the proliferation, migration and regenerative cellular properties following implantation of stem cells used in retinal or ocular diseases. Stem cell-based therapy is being pursued for treatment of retinal degenerative disease. Retinal stem cells have been isolated from several mammalian species, including humans. However, transplantation of these cells has been minimally successful due to the limited ability of the cells to migrate and integrate into the host retina. Bone marrow-derived stem cells may be an alternative, but bone marrow contains several types of pluripotent/multipotent cells, including hematopoietic stem cells, mesenchymal stem cells, and a heterogeneous population of non-hematopoietic cells that differentiate into mesenchymal tissues but possibly into other tissue types.

In at least some embodiments, the methods and devices described herein can be used in combination with compositions and methods applicable to cell-based or regenerative therapy for retinal diseases and disorders. In at least some embodiments, the methods and devices described herein can be used with pharmaceutical compositions, devices and methods for the regeneration or repair of retinal tissue using stem cells (e.g. Very Small Embryonic-like Stem cells (VSELs), mesenchymal stem cells, ectodermal stem cells, etc.). For example, the methods and devices described herein can be used in a method for treating a retinal disorder with PBM after administering to an individual in need thereof an ectodermal stem cell population to the individual's retinal tissue, and intravenously administering to the individual a mesenchymal stem cell population. The ectodermal stem cells may be derived from fetal neural tissue. In at least some embodiments, the methods and devices described herein can be used in deriving the mesenchymal stem cell population from a source selected from at least one of umbilical cord blood, adult bone marrow and placenta. In at least some embodiments, the methods and devices described herein can be used to treat one or more disease or disorders including, but not limited to, macular degeneration, retinitis pigmentosa, diabetic retinopathy, glaucoma or limbal epithelial cell deficiency. In at least some embodiments, the cells are induced in vitro to differentiate into a neural or epithelial lineage cells prior to administration and preconditioned with PBM. In other embodiments, the cells are administered with at least one other agent, such as a drug for ocular therapy, or another beneficial adjunctive agent such as an anti-inflammatory agent, anti-apoptotic agents, antioxidants or growth factors. In these embodiments, PBM treatment can be administered simultaneously with, or before, or after, the postpartum cells. The use of PBM may be used stimulate the regenerative aspects of the stem cells or use to supplement beneficial adjunctive therapeutic agents or both.

Another embodiment is a cell lysate prepared from mesenchymal stem cells or ectodermal stem cells that have been treated with PBM. The cell lysate, may be separated into a membrane enriched fraction and a soluble cell fraction. The present disclosure features the treatment of PBM to the cells in vitro prior to cell lysate preparation and prior to administration as well as after implantation into the patient.

Light Delivery Devices

The photobiotherapy methods for the treatment of ocular conditions, as described herein and in U.S. Provisional Patent Application No. 62/048,211, which was filed on Sep. 9, 2014, entitled MULTI-WAVELENGTH PHOTOTHERAPY SYSTEMS AND METHODS FOR THE TREATMENT OF DAMAGED OR DISEASED TISSUE, and incorporated herein by reference in its entirety, may be practiced and described using various light delivery systems. In one embodiment, the device is in a configuration conducive to office-based usage. The device may be self-standing or can be attached to an existing apparatus. This device may be augmented to include other diagnostic or therapeutic capabilities related to ocular disorders or to form a system with other devices.

The light delivery apparatus or device can be a floor, desk, cart, or table based unit. The device contains one or more light engines containing one or more light sources to deliver light of one or more selected wavelengths. The light from the sources can be combined using, for example, beam shaping optics, optical filters, light pipes, or combinations of these to achieve the desired spatial and spectral irradiance pattern at the eye. Other optical components may be included to guide the light from the light engine to the eye. In at least some embodiments, the device output is substantially spatially fixed, such that proper exposure of the target region requires the position of the patient to be manipulated and optimized. Such patient manipulation may be aided with the use of an adjustable chin rest or forehead rest or both. Fine spatial adjustment of the output may be accomplished through the use of, for example, moving elements (e.g., fold mirrors, etc.) within the device, actuated either manually or electrically. In other embodiments, the output of the device is substantially spatially adjustable. In this case, the device may contain a forehead or chin rest or both as a patient interface, and the output of the device may be adjusted to expose the target region. Large spatial adjustments can be accomplished with, for example, one or multiple optical elements (e.g., lenses, fold mirrors, etc.) translating or rotating to redirect the light to the target region. The adjustability may cover the expected range of positions for a single eye, or it may cover the range of positions expected for both eyes, eliminating the need to readjust a patient if treating both eyes sequentially.

As the device is suited for an office environment, it should be expected that a multitude of patients will interface with the device, and measures may be taken to limit cross-contamination between individuals. In at least some embodiments, removable forehead or chin rests can be provided that are either cleanable or disposable. In at least some embodiments, the forehead or chin rests may be protected by a cleanable or disposable barrier.

In at least some embodiments, the device contains an interface with which the user (doctor, practitioner, or patient) can initiate controls. This may include a touch screen or keyboard to select various treatment modalities, enter or extract data, perform device diagnostics, etc. A tangible or virtual joystick or other mechanism may be included to spatially adjust the system output.

FIGS. 1A-1D illustrate one embodiment of a light therapy device 100. The device 100 includes a housing 102, a patient interface surface 104, and at least one eyebox or eyepiece 106. The device also optionally includes a user interface 108, a power switch 110, a locking mechanism 112, and a beam positioning mechanism 114. The housing 102 holds the light engine and other optics, as described in more detail below. The illustrated housing 102 is one example of a housing, but it will be understood that other housing configurations can be used including a housing that attaches to, or supports, other optical devices.

The patient interface surface 104 is arranged so that the patient is positioned correctly to irradiate the eye or eyes of the patient with light therapy. The patient interface surface may be arranged to roughly fit the contours of the face of a patient and may include a disposable or cleanable surface to prevent or reduce patient cross-contamination.

The eyebox or eyepiece 106 may accommodate both eyes of the patient or only a single eye. In some embodiments, there may be separate eyeboxes or eyepieces for the right and left eyes. The eyebox or eyepiece 106 may have a peripheral region that is intended to contact the area around a patient's eye or the patient interface surface 104 may be sufficient to position the patient correctly to receive light therapy. The eyebox or eyepiece 106 may be simply an opening into which the patient positions his eye or the eyebox or eyepiece may include a lens or other optical components.

The optional user interface 108 can be built into the device and can be any suitable interface including, but not limited to, a touchscreen interface, a keyboard and display, or the like. Alternatively or additionally, the device 100 can include or permit a wired or wireless connection to an external user interface such, as for example, an external computer, a keyboard, a mouse or joystick, or the like. The user interface 108 is typically operated by the doctor or other practitioner, but, in some embodiments, there may be portions of the user interface that can be operated by the patient such as, for example, a button or other element for halting or starting light therapy. The user interface 108 may be used to input therapy parameters, patient information, operate the device 100, or any other suitable use. In some embodiments, the user interface 108 may also be coupled to an internal camera (for example, camera 754 of FIG. 7) so that the practitioner can view the patient's eye to aid in diagnosis or directing light therapy.

The optional power switch 110 can have any suitable form. The optional locking mechanism 112 may be provided to allow a user to lock operation of the device 100. The optional beam positioning mechanism 114 can be used to move the beam to interact with the patient's eye or eyes and can be any suitable mechanism including, but not limited to, a joy stick, a track ball, or a touchscreen.

FIG. 2 illustrates another embodiment of a device 200 that includes a housing 102, a patient interface surface 104, at least one eyebox or eyepiece 106, an optional user interface 108, an optional power switch 110, an optional locking mechanism 112, an optional beam positioning mechanism 114, and a chin rest 116. The chin rest 116 can have any suitable form and may have a surface that is disposable or cleanable to receive the chin of the patient. Preferably, the height of the chin rest relative to the remainder of the device is adjustable.

FIGS. 3A and 3B illustrate yet another embodiment of a device 300 that includes a housing 102, a patient interface surface 104, at least one eyebox or eyepiece 106, an optional user interface 108, an optional power switch 110, an optional locking mechanism 112, and an optional beam positioning mechanism 114. In this embodiment, the patient interface surface 104, as illustrated in FIGS. 3A and 3B, is removable so that it can be cleaned or replaced.

Figure 4:
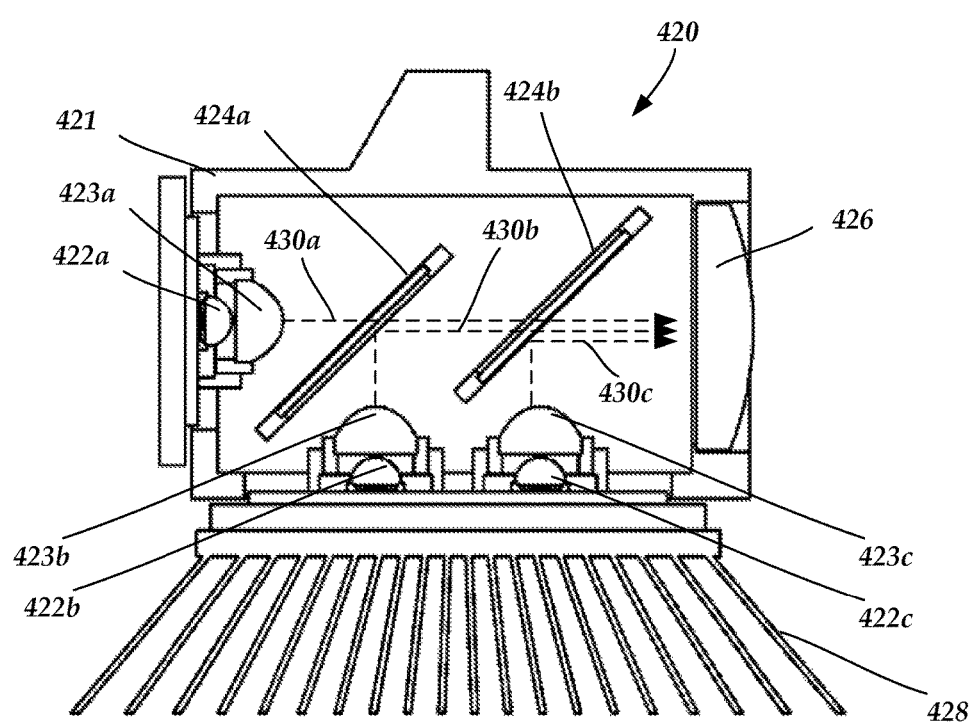
FIG. 4 is a schematic cross-sectional view of one embodiment of a light engine for use with a light therapy device, according to the present disclosure.

FIG. 4 illustrates one example of a light engine 420 for use with the device 100 (see, FIG. 1A) and positioned within the housing 102 (see, FIG. 1A) of the device 100. The light engine 420 includes an engine housing 421, one or more light sources 422a, 422b, 422c, one or more light directing components 424a, 424b, an optional lens 426, and an optional heat exchanger or heat sink 428. Light emitted from the light sources 422a, 422b, 422c forms light beams 430a, 430b, 430c, respectively.

Any suitable light source can be used including, but not limited to, light emitting diodes (LED), lamps, lasers, and the like. In at least some embodiments, one or more light emitting diodes are used. In other embodiments, one or more laser diodes are used. The one or more laser diodes can be gallium-aluminum-arsenic (GaAlAs) laser diodes, Aluminum gallium indium phosphide (AlGaLnP) laser diodes, diode-pumped solid state (DPSS) lasers, or vertical cavity surface-emitting laser (VCSEL) diodes, for example. In at least some embodiments where multiple light sources are used, the light sources can be coupled to one or more optical fibers. Other light sources that generate or emit light with an appropriate wavelength and irradiance can also be used. In some embodiments, a combination of multiple types of light sources can be used. Each light source can optionally include one or more of a lens (for example, lenses 423a, 423b, 423c), diffuser, waveguides, or other optical elements associated with the light source.

In some embodiments, the device may also include one or more non-light energy sources, such as magnetic energy sources, radio frequency sources, DC electric field sources, ultrasonic energy sources, microwave energy sources, mechanical energy sources, electromagnetic energy sources, and the like. For example, the phototherapy could be combined with OCT, PET, MRI, femtosensors, or the like to provide instruments with therapeutic, diagnostic, tracking or enhanced targeting capabilities.

In at least some embodiments with two or more light sources, the individual light sources are selected to generate light of different wavelengths. The wavelengths or ranges of wavelengths that are to be delivered to the eye are generated by the light sources, but can be filtered to remove some or all of the light of other wavelengths. In at least some embodiments, a first light source provides light of a first wavelength (which may be delivered with light of adjacent wavelengths or filtered to remove other light) and a second light source provides light of a second wavelength. In at least some embodiments, the first and second wavelengths differ by at least 25, 50, 75, 100, 150, 200, 250, 300, 400, or 500 nm. In some embodiments, a third light source provides light of a third wavelength and the third wavelength differs from the first and second wavelengths differ by at least 25, 50, 75, 100, 150, 200, 250, 300, 400, or 500 nm.

The light engine 420 includes one or more light directing components 424a, 424b. In the illustrated embodiment, light directing components 424a, 424b are reflective filters. Light directing component 424a is selected to pass light in light beam 430a having a first wavelength generated by first light source 422a and to reflect light in light beam 430b having a second wavelength generated by second light source 422b. Light directing component 424b is selected to pass light in light beam 430a having a first wavelength and light in light beam 430b having a second wavelength generated by second light source 422b. Light directing component 424b reflects light in light beam 430c having a third wavelength generated by second light source 422c. The light directing component 424b directs the desired wavelengths of light to lens 426.

Other light directing components can be used including, but not limited to, optical fibers, absorbing filters, reflective or absorbing polarizers, beamsplitters, and the like. In some embodiments, the device is operated so that two or more of the light sources generate light simultaneously. In other embodiments, the device operates to deliver light from a single light source at any given time, although the light sources may be turned on and off in any suitable light delivery sequence. The lens 426 can be a single lens or a combination of lenses and may include other optical components such as, for example, diffusers, apertures, filters, and the like.

Figure 5:
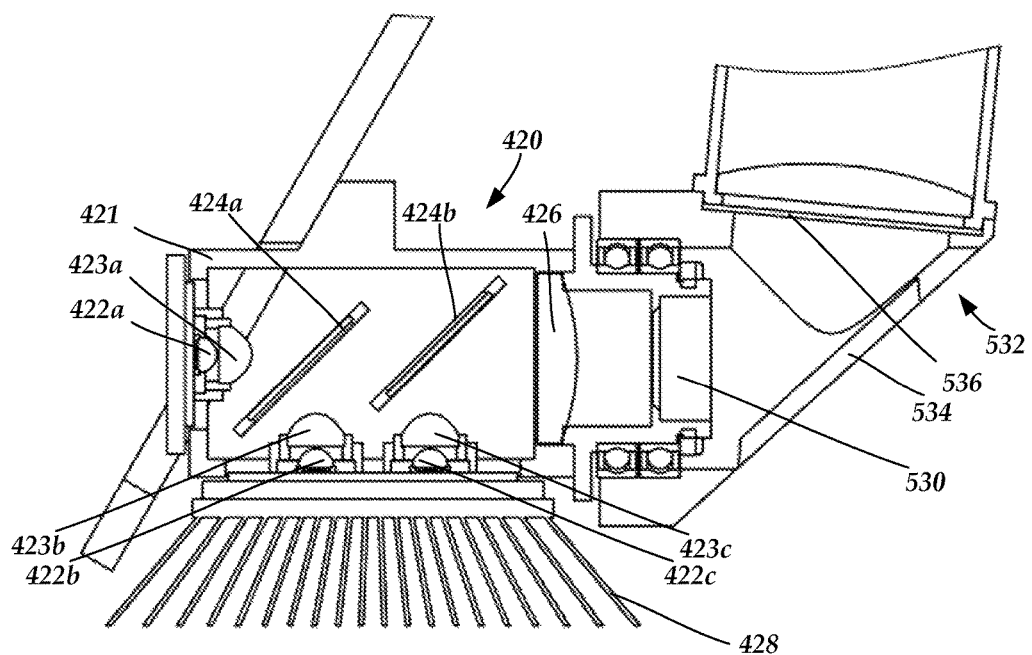
FIG. 5 is a schematic cross-sectional view of one embodiment of the light engine of FIG. 4 with additional optical components for use with a light therapy device, according to the present disclosure.

FIG. 5 illustrates the light engine 420 of FIG. 4 with additional optical components including an aperture 530 and a relay structure 532. The aperture 530 receives the light from the lens 426 and limits light directed to the eye of the patient. The relay structure 532 directs the light from the light engine 420 to the patient and can include any number of suitable components including, for example, one or more mirrors 534 and one or more lenses 536.

Figure 6A:
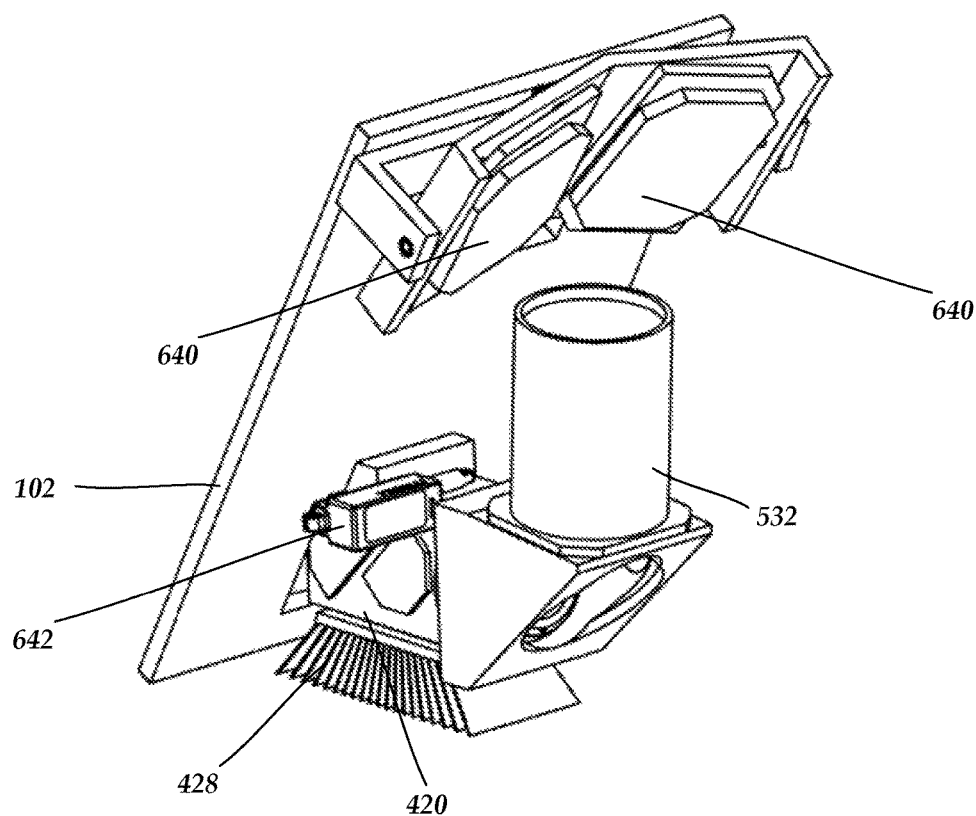
FIG. 6A is a side perspective view of one embodiment of optical components for use with a light therapy device, according to the present disclosure.
Figure 6B:
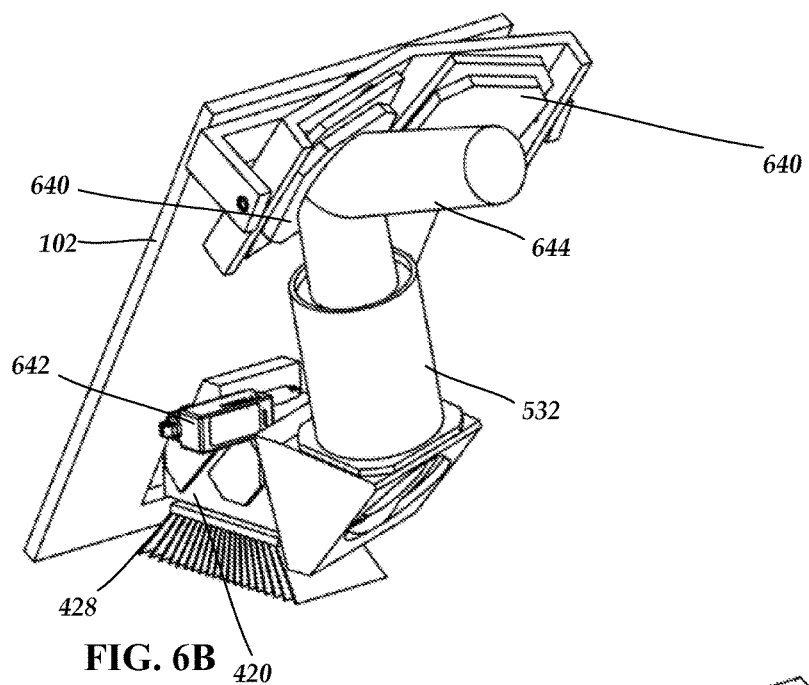
FIG. 6B is a side perspective view of the optical components of FIG. 6A with light directed to the left eye of a patient, according to the present disclosure.
Figure 6C:
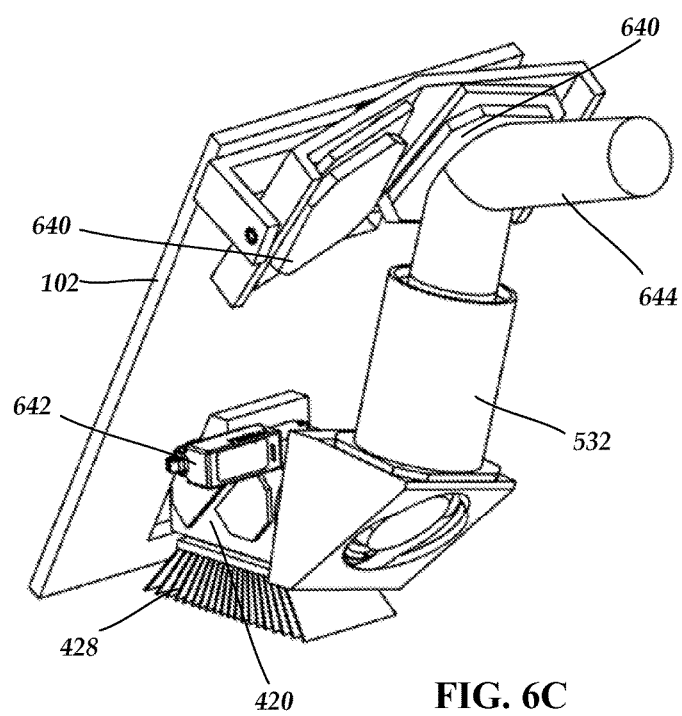
FIG. 6C is a side perspective view of the optical components of FIG. 6A with light directed to the right eye of a patient, according to the present disclosure.

FIGS. 6A-6C illustrate additional components of the device for delivery of light from the light engine 642 to the patient including a portion of the device housing 102, flow mirrors 640, and actuator 642. The actuator 642 can be used to rotate portions of the relay structure 532 (or even part of the light engine 420) to adjust the direction that the light beam 644 (FIGS. 6B and 6C) is directed. FIG. 6B illustrates a position with the light beam directed toward the left eye of the patient and FIG. 6C illustrates a position with the light beam directed toward the right eye of the patient. In some embodiments, the actuator 642 may simply have two positions. In other embodiments, the actuator 642 permits finer adjustment of the light beam position. In at least some embodiments, the actuator 642 is coupled to the user interface 108 or beam positioning mechanism 114 or both.

In at least some embodiments, the irradiance of the light beam is selected to provide a predetermined irradiance at the target ocular tissue. The target tissue may be an area of the eye affected by disease or trauma that has been identified using standard medical imaging techniques, it may be a portion of the eye that is known to be affected by a particular disease, it may be a portion of the eye that is known to control certain functions or process, or it may be any section of the eye. The selection of the appropriate irradiance of the light beam emitted from the emission surface to achieve a desired irradiance at the level of the target ocular tissue preferably includes, among other factors, the wavelength or wavelengths of light selected, the type of disease (if any), the clinical condition of the subject, and the distance to the target region.

In at least some embodiments with a plurality of light sources, certain light sources emit light at a higher or lower power as compared to other light sources. Power output of the light source can thus be tailored depending on the thickness of the eyelid, cornea, or other intervening tissue between the emission surface of the light source and the target ocular tissue. The parameters of the light emitted by the light sources are discussed in greater detail below.

Figure 8:
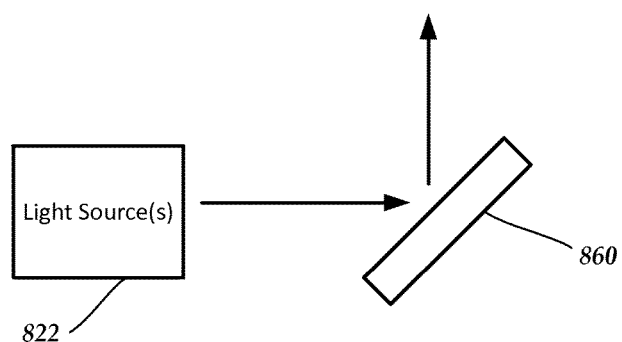
FIG. 8 is a schematic block diagram of the use of a spatial light modulator in the system for providing light therapy, according to the present disclosure.

In some embodiments, the device may also include a spatial light modulator to produce an image using the light from the light sources or to facilitate targeting of the light to a particular part of the eye (for example, the retina or a portion of the retina). FIG. 8 illustrates an arrangement with the light source(s) 822 with light directed to a spatial light modulator (SLM) 860 that modulates the light and directs the modulated light beam to the patient. The spatial light modulator 860 can be, for example, a liquid crystal on silicon (LCOS) display, a liquid crystal display (LCD), a micromirror array such as a digital light processor (DLP), a scan mirror, or any other suitable device that can reflect light and optionally can be used to form an image. The spatial light modulator may also include additional projection optics such as, lenses and the like. In at least some embodiments, the device may also utilize the lens of the patient's eye to also facilitate image formation.

The spatial light modulator may be reflective, as illustrated in FIG. 8, or transmissive in which the light is modulated as it is transmitted through the SLM. The spatial light modulator can be inserted at any suitable place along the light path. For example, a reflective SLM could be placed at the position of the fold mirror 534 in the embodiment illustrated in FIG. 5 or in any other suitable portion of the device. A transmissive SLM could be placed before or after the lens 426 or aperture 530 in the embodiment illustrated in FIG. 5 or in any other suitable portion of the device.

In at least some embodiments, targeting of the light source on a particular portion of the eye of the patient can be performed using the spatial light modulator, a camera to observe the patient's eye to allow manual or automatic adjust of the direction of the light beam, pupil tracking sensor, or any combination thereof.

Figure 7:
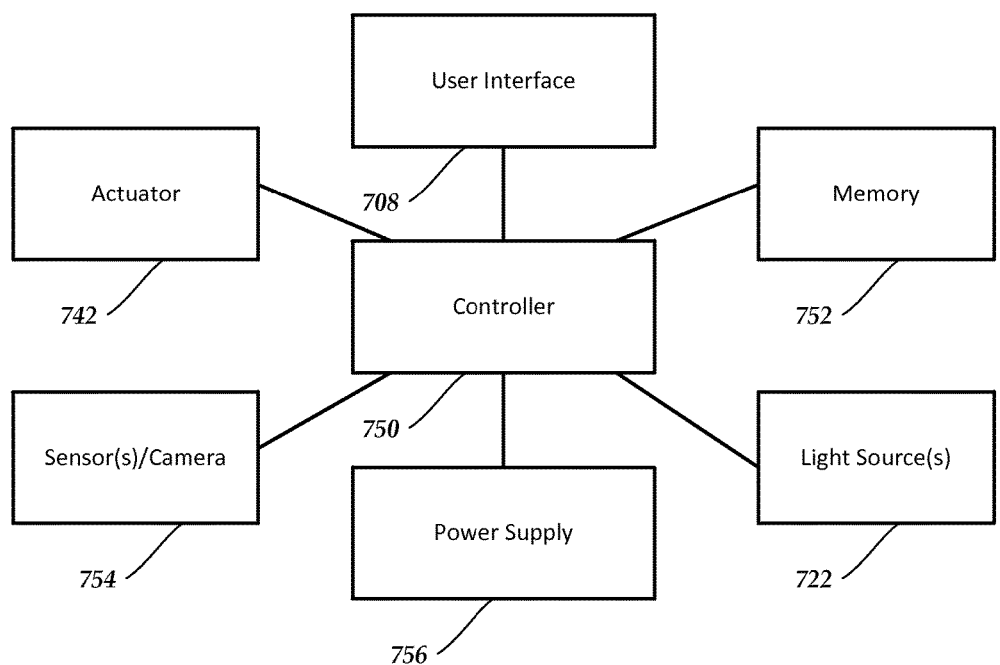
FIG. 7 is a schematic block diagram of components of one embodiment of a system for providing light therapy, according to the present disclosure.

FIG. 7 illustrates one embodiment of a system for operating the devices for treatment of ocular disease, disorders, degeneration, and the like. The system includes a controller 750, the user interface 708 (for example, user interface 108 of FIGS. 1A-3A), the actuator 742 (for example, actuator 642 of FIGS. 6A-6C), the light source(s) 722 (for example, light sources 422a, 422b, 422c of FIGS. 4 and 5), memory 752, one or more sensor(s)/camera 754, and a power supply 756. These components are described in more detail below. It will be recognized that other systems can include more or fewer components and that the components may be linked together in arrangements different from those illustrated in FIG. 7. For example, the spatial light modulator 860 of FIG. 8 can also be linked to the controller 750 of FIG. 7. In addition, any linkage between components can be through wired or wireless communication or any combination thereof.

Programmable Controller

To tailor one or more of the light energy emission, light energy intensity, light energy duration, frequency, area or sequence of application of light energy to a subject's ocular tissue, or other treatment parameters, at least some embodiments include a programmable controller (for example, controller 750 of FIG. 7) which may be part of user interface 708 or may be coupled to the user interface or may be separately coupled to the device. The programmable controller executes a set of program instructions that are stored in memory to accomplish tasks or operations such as, but not limited to, operating the one or more light sources according to a particular therapeutic regimen, communicating with external devices, monitoring the condition of elements such as the light sources and the power source, storing parameters or program instructions in the memory, and the like. For example, the programmable controller can be used to transmit light to specific target regions of the eye according to a therapeutic regimen. For example, the programmable controller can execute a treatment program that includes a set of activation times or periods during which each of the light sources is in an emitting state and a set of inactivation times or periods during which the light source is in a non-emitting state. In certain embodiments, the programmable controller comprises a general or a special purpose microprocessor. In at least some embodiments, the programmable controller can include an application-specific integrated circuit (ASIC) or Field Programmable Gate Array (FPGA).

In at least some embodiments, the programmable controller can communicate with internal memory (for example, memory 752 of FIG. 7) to retrieve or store data or program instructions for software or hardware. In at least some embodiments, the programmable controller comprises a central processing unit (CPU). The programmable controller can further include memory, such as random access memory (RAM) for temporary storage of information or flash memory, read only memory (ROM), EPROM memory, or EEPROM memory for permanent storage of information. In at least some embodiments, the memory can be reprogrammable after the initial programming. Additionally, the programmable controller can include a real time clock, one or more timers, an analog to digital (A/D) converter, a digital to analog (D/A) converter, a serial communications interface, such as $I^2C$ or Serial Peripheral Interface, a communications interface, or a pulse width modulation (PWM) generator. The power source can provide power to the programmable controller, which in turn can drive the one or more light sources. In at least some embodiments, the programmable controller drives the one or more light sources through a light source driver. The light source driver can provide an appropriate current or voltage level to energize the one or more light sources. When the programmable controller generates a control signal to drive a light source, light is emitted from the emission surface. In contrast, when the light source is not receiving a control signal from the programmable controller to generate light, the emission surface is in a non-emitting state. The light sources can be configured to emit light continuously or periodically in accordance with various therapeutic regimens.

In at least some embodiments, the programmable controller is preprogrammed (e.g., prior to implantation) with a desired set of treatment parameters for a given subject (e.g., patient). For example, a desired frequency of light energy emission (e.g., every 24 hours), duration of light energy emission (e.g., for 5 minutes), irradiance of light energy emission (e.g., from 1 mW to 10 mW), irradiation pattern or order of light source activity (e.g., a sequence of emission of light energy in those embodiments comprising more than one light source), and other parameters can be preprogrammed into the programmable controller. For pulsed light dosimetry, the treatment parameters can also include duty cycle, pulse shape, repetition rate, pulse width or irradiance per pulse for pulsed light dosimetry.

In at least some embodiments utilizing multiple light sources, the programmable controller can be programmed to activate a subset of the light sources to focus on a particular target region. In at least some embodiments, the programmable controller can be programmed to activate the light sources according to a predetermined treatment regimen, order, template, or sequence. For example, the treatment regimen can follow a pattern similar to the sequences described in paragraphs [0203]-[0228] of U.S. Patent Application Publication No. 2009/0254154, incorporated by reference herein. The treatment regimen can also be adjustable by a physician (e.g., via telemetry or a wireless or wired network interface).

In at least some embodiments, the programmable controller can be reprogrammed dynamically via a communications interface. The communications interface can comprise an antenna configured to receive RF communication from an external telemetry unit. The communications interface can also be configured to transmit information to the external telemetry unit. Other types of wireless communication links can also be used. In at least some embodiments, a physician can adjust treatment parameters in response to an alarm or warning generated by the light therapy apparatus. The physician can reprogram the programmable controller wirelessly via the communications interface.

In at least some embodiments, the programmable controller can automatically reprogram itself or recalibrate its treatment parameters in response to control signals received from feedback sensors (for example, sensor 754 of FIG. 7). The sensors can provide feedback regarding the parameters of the light treatment or the physiological parameters of the subject (e.g., patient). The sensors (for example, sensor 754 of FIG. 7) can include biomedical sensors, biochemical sensors, temperature sensors, and the like. In at least some embodiments, the sensors can be invasive sensors and can be implanted within the body, or attached to the body, at least temporarily. In at least some embodiments, the sensors can comprise noninvasive or minimally invasive sensors. The sensors can be used to measure, for example, adenosine triphosphate (ATP) levels or activity, optic nerve outputs waves (e.g., using an ERG sensor system), mitochondrial activity (e.g., by measuring NADH or NADPH levels), nitric oxide (NO) production or consumption, cytokines (such as IL-6 interleukins and tumor necrosis factors (TNF)), apoptotic markers (such as Bax and Bcl-2), evoked response optical scanning (EROS) responses, oxygen consumption levels, membrane potential, glycolysis activity, or pH levels. For example, increases in cellular ATP concentration and a more reduced state within the cell are both related to cellular metabolism and are considered to be indications that the cell is viable and healthy. The increased concentration of NADH within the targeted ocular tissue and a corresponding improvement in the redox state of the targeted ocular tissue reflects both the metabolic activities and the health of cells.

Diffusion

In at least some embodiments, the light source or the device includes one or more diffusers adapted to diffuse the light prior to reaching the eye or ocular tissue to advantageously homogenize the light beam. Generally, intervening tissues of the cornea are highly scattering which can reduce the impact of non-uniform beam intensity distributions on the illumination of the subject's retina. However, non-uniform beam intensity distributions with substantial non-homogeneities could result in some portions of the subject's eye being heated more than others (e.g., localized heating where a "hot spot" of the light beam impinges the subject's eye).

In at least some embodiments, the light source, or other components within the device, advantageously homogenizes the light beam to reduce non-uniformities. An example energy density profile of the light prior to being transmitted through the light source, is peaked at a particular emission angle. In at least some embodiments, after being diffused by the light source or other components in the device, the energy density profile of the light does not have a substantial peak at any particular emission angle, but is substantially evenly distributed among a range of emission angles. By diffusing the light, the light source or other components within the device distribute the light energy substantially evenly over the area to be illuminated, thereby controlling, inhibiting, preventing, minimizing, or reducing "hot spots" which would otherwise create temperature increases at the eye. Thus, by virtue of diffusing the light, the temperature of the irradiated portion of the subject's eye is lower than it would otherwise be if the device did not diffuse the light. For example, by diffusing the light, the temperature of the irradiated portion of the subject's eye can be higher than the temperature of the portion of the subject's eye if it were not irradiated, but lower than the temperature of the portion of the subject's eye if it were irradiated but the light were not diffused. In addition, by diffusing the light prior to reaching the eye, the device can effectively increase the spot size of the light impinging the eye, thereby advantageously lowering the irradiance at the eye.

In at least some embodiments, the light source or other components in the device provide sufficient diffusion of the light such that the irradiance of the light is less than a maximum tolerable level of the eye, or other ocular tissue. For example, the maximum tolerable level of certain embodiments is a level at which the subject experiences discomfort or pain, while in certain other embodiments, the maximum level is a level at which the subject's eye or ocular tissue is damaged (e.g., thermal damage or burned). In at least some embodiments, the device provides sufficient diffusion of the light such that the irradiance of the light equals a therapeutic value at the target tissue. The device can include diffusers such as, but are not limited to, holographic diffusers such as those available from Physical Optics Corp. of Torrance, Calif. and Display Optics P/N SN1333 from Reflexite Corp. of Avon, Conn.

Targeting

Light therapy may be administered through a closed eyelid, in which much of the light can be expected to scatter over a relatively broad area of the retina, or it may be administered to the open eye. In the case of the open eye, it is expected that the majority of the therapeutic light will be delivered to the retina through the lens and pupil of the eye with minimal scattering. In certain embodiments, the device includes the ability to target specific areas of the retina through the pupil. This can be accomplished through the inclusion of a Spatial Light Modulator (SLM) to precisely shape and control the exposed area on the retina. The SLM may be an LCOS panel, scanning mirror, deformable mirror array, or other modulation device.

In at least some embodiments, the SLM, in combination with illumination and imaging optics, provides static or moving images to the patient. The images may be used to aid in the control of the treated eye's focus and orientation during therapy by directing the patient's gaze, or they may function to increase the usability of the device by providing visual entertainment to the patient during therapy. In certain embodiments, the illumination source of the SLM is used only for image display, while therapy is provided via a secondary light source or sources. In other embodiments, the SLM illumination source, or sources, provides the therapy.

Feedback

In at least some embodiments, the programmable controller includes a logic circuit, a clock coupled to the logic circuit, and an interface coupled to the logic circuit. The clock of at least some embodiments provides a timing signal to the logic circuit so that the logic circuit can monitor and control timing intervals of the applied light. Examples of timing intervals include, but are not limited to, total treatment times, pulse width times for pulses of applied light, and time intervals between pulses of applied light. In at least some embodiments, the light source can be selectively turned on and off to reduce the thermal load on the eye or ocular tissue and to deliver a selected irradiance to particular areas of the eye or other ocular tissue.

The interface of at least embodiments provides signals to the logic circuit, which the logic circuit uses to control the applied light. The interface can comprise a user interface or an interface to a sensor (for example, sensor 754 of FIG. 7) monitoring at least one parameter of the treatment. In at least some embodiments, the programmable controller is responsive to signals from the sensor to preferably adjust the treatment parameters to optimize the measured response. The programmable controller can thus provide closed-loop monitoring and adjustment of various treatment parameters to enhance or optimize the phototherapy. The signals provided by the interface from a user are indicative of parameters that may include, but are not limited to, individual subject characteristics (e.g., eye lid skin type, fat percentage), selected applied irradiances, target time intervals, and irradiance/timing profiles for the applied light.

In at least some embodiments, the logic circuit is coupled to a light source driver. The light source driver is coupled to a power supply (for example, power supply 756 of FIG. 7), which in at least some embodiments is a battery or capacitive energy storage device and in other embodiments includes an alternating current source. The light source driver is also coupled to the light source. The logic circuit is responsive to the signal from the clock and to user input from the user interface to transmit a control signal to the light source driver. In response to the control signal from the logic circuit, the light source driver adjusts and controls the power applied to the light source. In at least some embodiments, the control circuit can be used to provide real-time positive or negative feedback.

In at least some embodiments, the logic circuit is responsive to signals from a sensor monitoring at least one parameter of the treatment to control the applied light. For example, at least embodiments include a temperature sensor in thermal communication with the skin or eyelid to provide information regarding the temperature of the skin to the logic circuit. In at least some embodiments, the logic circuit is responsive to the information from the temperature sensor to transmit a control signal to the light source driver so as to adjust the parameters of the applied light to maintain the skin or eyelid temperature below a predetermined level. Other examples of suitable sensors include other biomedical sensors including, but not limited to, a blood flow sensor, a blood gas (e.g., oxygenation, femtosensor) sensor, an ATP production sensor, or a cellular activity sensor. Such biomedical sensors can provide real-time feedback information to the logic circuit. For example, if ATP production or mitochondrial activity levels are below a certain threshold level, the logic circuit can generate a control signal to the light source(s) to adjust a treatment parameter of the applied light, such as a treatment time, wavelength, irradiance level, or other parameter. In at least some embodiments, the logic circuit is responsive to signals from a sensor or sensors to preferably adjust the parameters of the applied light to enhance or optimize the measured response. The logic circuit can thus provide automatic real-time closed-loop monitoring and adjustment of various parameters of the applied light to enhance or optimize the phototherapy. In other embodiments, the control circuit can be configured to provide manual closed-loop feedback. The sensors (for example, sensor 754 of FIG. 7) can also include biochemical sensors, EEG sensors, EROS sensors, photosensors, or other sensors. Any sensor or combination of sensors can be used.

In at least some embodiments, the device provides a method for imaging the patient's sclera, cornea, retina, or other portion of the eye. Such an image may be obtained by directing a patient's gaze toward a specified point or other region, and then viewing or capturing an image of the desired area of the eye. In at least some embodiments, this is performed in an automated fashion, with the device automatically adjusting the focus, exposure, size, or location for the image. In at least some embodiments, the user manually determines one or more of the image capturing parameters. In at least some embodiments, information from the image is then used by the user of the device to identify and establish specific treatment or target areas of the eye. In at least some embodiments, the user manually adjusts the device output such that the desired dosage is delivered to the target areas. In at least some embodiments, the target areas are programmed into the device, and the logic circuit may then dynamically adjust the device output to deliver the desired therapy to the identified regions.

In at least some embodiments, the logic circuit is responsive to signals indicating the spatial position or orientation of the patient's eye (e.g., where the patient is looking) This may be accomplished through the use of one or more cameras (for example, camera 754 of FIG. 7) and associated software algorithms. Supplementary emitters in infrared or other wavelengths may be used as illumination sources to facilitate the eye-tracking. Alternatively, commercially available eye-tracking components or algorithms may be incorporated into the device, partially or in entirety. In at least some embodiments, the logic circuit may utilize the eye-orientation signal to adjust the device output spatially to maintain the appropriate exposure on previously identified target areas. In at least some embodiments, it may use the signal to adjust the intensity of the device output. Such intensity modulation may include increasing or decreasing the device output to maintain the appropriate exposure to a given area, or it may include the temporary cessation of therapy.

In at least some embodiments, the device actively monitors the state of the patient's eyelid (e.g., open or closed) during therapy. In at least some embodiments, the signal is used as an interlock in the logic circuit, temporarily stopping output of the device if a particular eyelid state is detected. In at least some embodiments, the signal is used by the logic circuit to increase or decrease the power output of the device. The logic circuit may include a measurement of the cumulative time that a particular eyelid state exists over the course of a treatment. The total treatment time may then be automatically adjusted to deliver the total desired dosage. In at least some embodiments in which the therapy is nominally delivered through the closed eye, the logic circuit may halt therapy whenever an open-eye state is detected, or it may temporarily reduce the device output to maintain a constant irradiance on the retina or other portion of the eye. In at least some embodiments in which therapy is nominally delivered to an open eye, the logic circuit may halt therapy whenever a closed-eye state is detected, or it may temporarily increase the device output to maintain a constant irradiance on the retina or other portion of the eye.

In at least some embodiments, the device contains one or more cameras (for example, camera 754 of FIG. 7) and associated software algorithms for measuring the diameter of a patient's pupil. This measurement may be performed once, periodically, or continually. The logic circuit may then use the pupil diameter measurement signal to adjust treatment parameters to achieve the desired dosage on the retina.

In at least some embodiments, the device contains sensors (for example, sensor 754 of FIG. 7) to monitor the spatial or temporal irradiance pattern delivered to the patient. The sensor may include an array of one or more photodiodes, a camera of appropriate wavelength and time sensitivity, or another sensor capable of measuring the spatial and temporal irradiance profile of the delivered therapy. The resulting "beam profile" may then be analyzed through software within to the device to determine specific characteristics of the delivered therapy, including one or more of the following: diameter (as defined by a relative encircled energy metric, or a relative intensity metric), uniformity, pulse frequency, total power, maximum intensity, etc. In at least some embodiments, the logic circuit periodically or continuously monitors the beam profile as a method to validate of the delivered therapy. In at least some embodiments, the logic circuit uses the beam profile data as feedback to modulate the output of the device to achieve the desired dosage.

Pupil Dilation Monitoring

In addition to tracking the eye movement, targeting the retina, aiming the beam, and confirming eyelid position, monitoring the pupil diameter may be used to ensure the chosen beam diameter is not clipped by the pupil during therapy. If the pupil diameter were to constrict, the expected dose may not reach the target tissue. Applying pupil dilation solutions may not be desired for this therapy. Controlling pupil diameter via ambient light intensity may not be reliable or practical for this application since visible light of a defined intensity is part of the therapy. Estimating a single value for minimum pupil diameter across all patient populations may not be practical or allow all targeted tissues to be accessed through the pupil.

Light Intensity Sensors to Map Application of Light to Target Surface

In at least some embodiments, the device may include complex measurements and algorithms for monitoring light intensity. Confirmatory measurements may be prudent risk mitigations. For example, the beam profile exiting the device may be measured to confirm select parameters are being applied to the subject as intended (beam diameter, beam intensity map). In at least some embodiments, the device may reflect the beam off a 'leaky' mirror prior to exiting the device. The small amount of light penetrating the 'leaky' mirror can be sampled by a sensor array (for example, sensor 754 of FIG. 7) to measure the selected parameters. In at least some embodiments, a camera (for example, camera 754 of FIG. 7) can monitor light reflected from the patient. The reflected light could be sampled to identify the beam profile applied to the patient.

The various parameters of the light beam emitted from the emission surface are selected to provide treatment while controlling, inhibiting, preventing, minimizing, or reducing injury or discomfort to the subject due to heating of the skin or eye tissue by the light. While discussed separately, these various parameters below can be combined with one another within the disclosed values in accordance with embodiments described herein.

Wavelength

In at least some embodiments, light in the visible to near-infrared wavelength range is used to irradiate the subject's skin or eye tissue. In at least some embodiments, the light from a particular light source is substantially monochromatic (i.e., light having one wavelength, or light having a narrow band of wavelengths). In at least some embodiments, the desired beneficial or therapeutic biological response is established with the use of one or more selected wavelengths. In at least some embodiments, the light includes one or more wavelengths between 550 nanometers and 1064 nanometers, or between 590 nanometers and 980 nanometers. In at least some embodiments, multiple wavelengths are used (e.g. applied concurrently or sequentially). In at least some embodiments, the light of a particular desired wavelength has a wavelength distribution peaked at a peak wavelength and has a line width less than ±10 nanometers from the peak wavelength. In at least some embodiments, the light of a particular desired wavelength has a line width less than 4 nanometers, full width at 90% of energy. In at least some embodiments, the one or more chosen wavelength are selected from 590 nm±10%, 670 nm±10%, 810 nm±10%, and 1064 nm±10%, with a spectral line width less than 4 nanometers, full width at 90% of energy. In at least some embodiments, the light of a particular desired wavelength has a wavelength distribution peaked at a peak wavelength and has a line width less than ±40 nanometers from the peak wavelength at 50% of energy. In at least some embodiments, the one or more chosen wavelength are selected from 590 nm±10%, 670 nm±10%, 810 nm±10%, and 1064 nm±10%, with a spectral line width less than 40 nanometers, full width at 50% of energy.

In at least some embodiments, the selected wavelength is in a range from 800 to 900 nm including, for example, a range of 850 nm±10, 15, or 30 nm. In at least some embodiments, the selected wavelength is in a range from 600 to 700 nm including, for example, a range of 660±10, 15, or 30 nm. In at least some embodiments, the selected wavelength is in a range from 550 to 650 nm including, for example, a range of 590±10, 15, or 30 nm. In at least some embodiments, the device produces multiple wavelengths of light including, but not limited to, any combination of the wavelengths or wavelength ranges identified in this or the preceding paragraph.

In at least some embodiments, each preselected wavelength of the light is selected to be at or near a transmission peak (or at or near an absorption minimum) for the intervening tissue. In at least some embodiments, one wavelength corresponds to a peak in the transmission spectrum of tissue at or 820 nanometers (NIR). In at least some embodiments, one wavelength corresponds to a peak in the transmission spectrum of tissue at or 670 nanometers (red visible).

In at least some embodiments, the light source includes at least one continuously emitting GaAlAs laser diode having a wavelength chosen from the previous list.

In at least some embodiments, the light source includes at least one LED, which each provide non-coherent light, having a wavelength chosen from the previous list.

In at least some embodiments, the one or more wavelengths are selected so as to work with one or more photoacceptors within the target tissue. Without being bound by theory or by a specific mechanism, it is believed that irradiation of one or more CCO photoacceptors for example, increases the production of ATP in the target tissue or controls, inhibits, prevents, minimizes, or reduces apoptosis of the injured tissues, thereby producing beneficial effects, as described more fully elsewhere. Other wavelengths may be chosen to work with photoacceptors to control, inhibit, or stimulate distinct biological responses in the target tissue.

Some photoacceptors, such as water or hemoglobin, are ubiquitous and absorb light to such a degree that little or no penetration of light energy into a tissue occurs. For example, water absorbs light above approximately 1300 nanometers. Thus, energy in this range has little ability to penetrate tissue due to the water content. However, water is transparent or nearly transparent in wavelengths between 300 and 1300 nanometers. Another example is hemoglobin, which absorbs heavily in the region between 300 and 670 nanometers, but is reasonably transparent above 670 nanometers. Based on these broad assumptions, one can define an "IR window" into the body. Within the window, there are certain wavelengths that are more or less likely to penetrate.

Irradiance or Power Density

In at least some embodiments, the light sources emit a light beam having a time-averaged irradiance, or power density, at the emission surface of the light sources (e.g., at the retinal surface) between 0.005 mW/cm$^2$ to 10 W/cm$^2$, 0.01 mW/cm$^2$ to 5 W/cm$^2$, 0.01 mW/cm$^2$ to 1 W/cm$^2$, 1 mW/cm$^2$ to 500 mW/cm$^2$, 500 mW/cm$^2$ to 1 W/cm$^2$, or overlapping ranges thereof, across the cross-sectional area of the light beam. In at least some embodiments, the time-averaged irradiance at the target tissue is at least 0.001 mW/cm$^2$ and up to 1 W/cm$^2$ at the level of the tissue. In at least some embodiments, the time-averaged subsurface irradiance at the target tissue is at least 0.001, 0.005, 0.01, 0.05, 0.1, 0.5, 1, 5, 10, 15, 20, 30, 40, 50, 60, 70, 80, 90, 100, 200, 300, 400, 500, 600, 700, 800, 900, or 1000 mW/cm$^2$, or greater, depending on the desired clinical performance.

For a pulsed light beam, the time-averaged irradiance is averaged over a long time period compared to the temporal pulse widths of the pulses (e.g., averaged over a fraction of a second longer than the temporal pulse width, over 1 second, or over multiple seconds). For a continuous-wave (CW) light beam with time-varying irradiance, the time-averaged irradiance can be an average of the instantaneous irradiance averaged over a time period longer than a characteristic time period of fluctuations of the light beam. In at least some embodiments, a duty cycle in a range between 1% and 80%, between 10% and 30%, or 20% can be used with a peak irradiance at the target tissue of 0.001 mW/cm$^2$ to 1 W/cm$^2$, 0.01 mW/cm$^2$ to 500 mW/cm$^2$, 10 mW/cm$^2$ to 100 mW/cm$^2$, or 25 mW/cm$^2$ to 125 mW/cm$^2$. For example, in at least some embodiments, a pulsed dosimetry having a 20% duty cycle and a 50 mW/cm$^2$ is used. In at least some embodiments, the pulsed light beam has an energy or fluence per pulse (e.g., peak irradiance multiplied by the temporal pulse width) at the emission surface of the light source between 0.001 µJ/cm$^2$ to 150 J/cm$^2$, between 0.01 µJ/cm$^2$ to 5 J/cm$^2$, between 0.1 µJ/cm$^2$ to 1 J/cm$^2$, between 0.01 mJ/cm$^2$ to 100 mJ/cm$^2$, between 100 mJ/cm$^2$ to 1 J/cm$^2$, or overlapping ranges thereof.

The cross-sectional area of the light beam of at least some embodiments (e.g., multimode beams) can be approximated using an approximation of the beam intensity distribution. For example, as described more fully below, measurements of the beam intensity distribution can be approximated by a Gaussian (1/e$^2$ measurements) or by a "top hat" distribution and a selected perimeter of the beam intensity distribution can be used to define a bound of the area of the light beam. In at least some embodiments, the irradiance at the emission surface is selected to provide the desired irradiances at the target tissue. The irradiance of the light beam is preferably controllably variable so that the emitted light energy can be adjusted to provide a selected irradiance at the tissue being treated. In at least some embodiments, the light beam emitted from the emission surface is continuous with a total radiant power in a range of 4 Watts to 6 Watts. In at least some embodiments, the radiant power of the light beam is 5 Watts±20% (CW). In certain embodiments, the peak power for pulsed light is in a range of 10 Watts to 30 Watts (e.g., 20 Watts). In at least some embodiments, the peak power for pulsed light multiplied by the duty cycle of the pulsed light yields an average radiant power in a range of 4 Watts to 6 Watts (e.g., 5 Watts).

In at least some embodiments, the irradiance of the light beam is selected to provide a predetermined irradiance at the target tissue (e.g., at a depth of the retinal pigmented epithelial layer). The selection of the appropriate irradiance of the light beam emitted from the emission surface to use to achieve a desired target tissue irradiance preferably includes consideration of scattering by other intervening tissues. Further information regarding the scattering of light by tissue is provided by U.S. Pat. No. 7,303,578 and V. Tuchin in "Tissue Optics: Light Scattering Methods and Instruments for Medical Diagnosis," SPIE Press (2000), Bellingham, Wash., pp. 3-11, which are incorporated herein by reference.

Phototherapy for the treatment of ocular conditions (e.g., glaucoma, AMD, diabetic retinopathy, retinitis pigmentosa, CRS, NAION, Leber's disease, ocular surgery, and uveitis) may depend, at least in part, on the irradiance or power density (i.e., power per unit area or number of photons per unit area per unit time) and energy density (i.e., energy per unit area or number of photons per unit area) of the light energy applied to tissue in determining the relative efficacy of phototherapy. This may be particularly applicable with respect to treating and saving surviving but endangered cells in a zone of danger surrounding the primary injury. In at least some embodiments, given a selected wavelength of light energy, it is the irradiance or the energy density of the light delivered to tissue (as opposed to the total power or total energy delivered to the tissue) that may determine the relative efficacy of phototherapy.

Without being bound by theory or by a specific mechanism, it is believed that light energy delivered within a certain range of irradiances and energy densities provides the desired biostimulative effect on the intracellular environment, such that proper function is returned to previously nonfunctioning or poorly functioning mitochondria in at-risk cells. The biostimulative effect may include interactions with targeted photoacceptors within the target tissue, some which facilitate production of ATP or controls, inhibits, prevents, minimizes, or reduces apoptosis of the injured cells which have experienced disease, ageing or decreased blood flow (e.g., due to the ischemia).

In at least some embodiments, delivering the cytoprotective amount of light energy includes selecting a surface irradiance of the light energy at the eyelid or corneal surface corresponding to the predetermined irradiance at the target area of the eye (e.g. retina). As described above, light propagating through tissue is scattered and absorbed by the tissue. Calculations of the irradiance to be applied to the eyelid or corneal surface so as to deliver a predetermined irradiance to the selected target area of the eye may take into account the attenuation of the light energy as it propagates through intervening tissue. Factors known to affect the attenuation of light propagating to the eye from the skin include, but are not limited to, skin thickness, subject's age and gender, and the location of the target area of the eye, particularly the depth of the area relative to the surface of the skin or cornea.

The irradiance selected to be applied to the target area of the subject's eye may depend on a number of factors, including, but not limited to, the wavelength of the applied light, heating considerations, and the subject's clinical condition, including the extent of the affected tissue area. The irradiance or power density of light energy to be delivered to the target area of the subject's eye may also be adjusted to be combined with any other therapeutic agent or agents, especially pharmaceutical neuroprotective agents, to achieve the desired biological effect. In such embodiments, the selected wavelengths and irradiance may also depend on the additional therapeutic agent or agents chosen.

Temporal Pulse Width, Temporal Pulse Shape, Duty Cycle, Repetition Rate, and Irradiance Per Pulse A generalized temporal profile of a pulsed light beam in accordance with at least some embodiments is described herein. The temporal profile includes multiple pulses ($P_1$, $P_2, \ldots, P_i$), each pulse having a temporal pulse width during which the instantaneous intensity or irradiance $I(t)$ of the pulse is substantially non-zero. For example, for the pulsed light beam, pulse $P_1$ has a temporal pulse width from time $t=0$ to time $t=T_1$, pulse $P_2$ has a temporal pulse width from time $t=T_2$ to time $t=T_3$, and pulse $P_i$ has a temporal pulse width from time $t=T_i$ to time $t=T_{i+1}$. The temporal pulse width can also be referred to as the "pulse ON time." The pulses are temporally spaced from one another by periods of time during which the intensity or irradiance of the beam is substantially zero. For example, pulse $P_1$ is spaced in time from pulse $P_2$ by a time $t=T_2-T_1$. The time between pulses can also be referred to as the "pulse OFF time." In at least some embodiments, the pulse ON times of the pulses are substantially equal to one another, while in other embodiments, the pulse ON times differ from one another. In at least some embodiments, the pulse OFF times between the pulses are substantially equal to one another, while in other embodiments, the pulse OFF times between the pulses differ from one another. As used herein, the term "duty cycle" has its broadest reasonable interpretation, including but not limited to, the pulse ON time divided by the sum of the pulse ON time and the pulse OFF time. For a pulsed light beam, the duty cycle is less than one. The values of the duty cycle and the temporal pulse width fully define the repetition rate of the pulsed light beam.

Each of the pulses can have a temporal pulse shape which describes the instantaneous intensity or irradiance of the pulse $I(t)$ as a function of time. For example, the temporal pulse shapes of the pulsed light beam are irregular, and are not the same among the various pulses. In at least some embodiments, the temporal pulse shapes of the pulsed light beam are substantially the same among the various pulses. For example, the pulses can have a square temporal pulse shape, with each pulse having a substantially constant instantaneous irradiance over the pulse ON time. In at least some embodiments, the peak irradiances of the pulses differ from one another, while in other embodiments, the peak irradiances of the pulses are substantially equal to one another. Various other temporal pulse shapes (e.g., triangular, trapezoidal) are also compatible with at least some embodiments. In at least some embodiments, the rise time and the fall time can be expressed relative to a specified fraction of the peak irradiance of the pulse (e.g., time to rise/fall to 50% of the peak irradiance of the pulse).

In at least some embodiments, the peak irradiance of a pulse $P_i$ can be the maximum value of the instantaneous irradiance $I(t)$ during the temporal pulse width of the pulse. In at least some embodiments, the instantaneous irradiance is changing during the temporal pulse width of the pulse, while in other embodiments, the instantaneous irradiance is substantially constant during the temporal pulse width of the pulse.

In at least some embodiments, pulse irradiance $I_{P_i}$ of a pulse $P_i$ can be the integral of the instantaneous irradiance $I(t)$ of the pulse $P_i$ over the temporal pulse width of the pulse:

$$I_{P_i} = \int_{T_i}^{T_{i+1}} I(t) \cdot dt / (T_{i+1} - T_i).$$

In at least some embodiments, total irradiance $I_{TOTAL}$ can be the sum of the pulse irradiances of the pulses:

$$I_{TOTAL} = \sum_{i=0}^{N} I_{P_i}.$$

In at least some embodiments, time-averaged irradiance $I_{AVE}$ can be the integral of the instantaneous irradiance $I(t)$ over a period of time T large compared to the temporal pulse widths of the pulses:

$$I_{AVE} = \int_0^T I(t) \cdot dt / T.$$

The integral $$\int_0^T I(t) \cdot dt$$

provides the energy of the pulsed light beam.

For example, for a plurality of square pulses with different pulse irradiances $I_{P_i}$ and different temporal pulse widths $\Delta T_i$, the time-averaged irradiance over a time T equals $$I_{AVE} = \frac{1}{T} \sum_i I_{P_i} \cdot \Delta T_i.$$

For another example, for a plurality of square pulses with equal pulse irradiances $I_P$, with equal temporal pulse widths, and equal pulse OFF times (having a duty cycle D), the time-averaged irradiance equals $I_{AVE}=I_P \cdot D$.

The pulse irradiances and the duty cycle can be selected to provide a predetermined time-averaged irradiance. In at least some embodiments in which the time-averaged irradiance is equal to the irradiance of a continuous-wave (CW) light beam, the pulsed light beam and the CW light beam have the same number of photons or flux as one another. For example, a pulsed light beam with a pulse irradiance of 5 mW/cm$^2$ and a duty cycle of 20% provides the same number of photons as a CW light beam having an irradiance of 1 mW/cm$^2$. However, in contrast to a CW light beam, the parameters of the pulsed light beam can be selected to deliver the photons in a manner which achieve results which are not obtainable using CW light beams.

In at least some embodiments, one or more of the temporal pulse width, temporal pulse shape, duty cycle, repetition rate, and pulse irradiance of the pulsed light beam are selected such that no portion of tissue is heated to a temperature greater than 60 degrees Celsius, greater than 55 degrees Celsius, greater than 50 degrees Celsius, or greater than 45 degrees Celsius. In at least some embodiments, one or more of the temporal pulse width, temporal pulse shape, duty cycle, repetition rate, and pulse irradiance of the pulsed light beam are selected such that no portion of tissue is heated to a temperature greater than 30 degrees Celsius above its baseline temperature, greater than 20 degrees Celsius above its baseline temperature, or greater than 10 degrees Celsius above its baseline temperature. In at least some embodiments, one or more of the temporal pulse width, temporal pulse shape, duty cycle, repetition rate, and pulse irradiance of the pulsed light beam are selected such that no portion of the tissue is heated to a temperature greater than 5 degrees Celsius above its baseline temperature, greater than 3 degrees Celsius above its baseline temperature, or greater than 1 degree Celsius above its baseline temperature. In at least some embodiments, the baseline temperature is the temperature at which the tissue would have if it were not irradiated by the light. In contrast to previous low-light level therapies, the pulsed light beam has an average radiant power in the range of 1 Watt to 10 Watts or in a range of 4 Watts to 6 Watts.

In at least some embodiments, pulsed irradiation may provide a more efficacious treatment. The pulsed irradiation can provide higher peak irradiances for shorter times, thereby providing more power to propagate to the target tissue while allowing thermal relaxation of the intervening tissue and blood between pulses to avoid unduly heating the intervening tissue. The time scale for the thermal relaxation is typically in the range of a few milliseconds. For example, the thermal relaxation time constant (e.g., the time for tissue to cool from an elevated temperature to one-half the elevated temperature) of human skin is about 3-10 milliseconds, while the thermal relaxation time constant of human hair follicles is about 40-100 milliseconds.

However, while pulsed light of this time scale advantageously reduces the heating of intervening tissue and blood, it does not provide an optimum amount of efficaciousness as compared to other time scales. In at least some embodiments, the subject's eye or ocular tissue is irradiated with pulsed light having parameters which are not optimized to reduce thermal effects, but instead are selected to stimulate, to excite, to induce, or to otherwise support one or more intercellular or intracellular biological processes which are involved in the survival, regeneration, or restoration of performance or viability of cells. Thus, In at least some embodiments, the selected temporal profile can result in temperatures of the irradiated tissue which are higher than those resulting from other temporal profiles, but which are more efficacious than these other temporal profiles. In at least some embodiments, the pulsing parameters are selected to utilize the kinetics of the biological processes rather than optimizing the thermal relaxation of the tissue. In at least some embodiments, the pulsed light beam has a temporal profile (e.g., peak irradiance per pulse, a temporal pulse width, and a pulse duty cycle) selected to modulate membrane potentials in order to enhance, restore, or promote cell survival, cell function, or both of the irradiated cells following the ocular disease or injury. For example, in at least some embodiments, the pulsed light has a temporal profile which supports one or more intercellular or intracellular biological processes involved in the survival or regeneration of retinal cells, but does not optimize the thermal relaxation of the irradiated tissue. In at least some embodiments, the cells survive longer after the irradiation as compared to their survival if the irradiation did not occur. For example, the light of at least some embodiments can have a protective effect on the cells, or can cause a regeneration process in the cells.

In at least some embodiments, the temporal profile (e.g., peak irradiance, temporal pulse width, and duty cycle) is selected to utilize the kinetics of the biological processes while maintaining the irradiated portion of the tissue at or below a predetermined temperature. This predetermined temperature is higher than the temperature which could be achieved for other temporal profiles (e.g., other values of the peak irradiance, temporal pulse width, and duty cycle) which limit or minimize the temperature increase of surrounding tissue due to the irradiation. For example, a temporal profile having a peak irradiance of 10 W/cm$^2$ and a duty cycle of 20% has a time-averaged irradiance of 2 W/cm$^2$. Such a pulsed light beam provides the same number of photons to the irradiated surface as does a continuous-wave (CW) light beam with an irradiance of 2 W/cm$^2$. However, because of the "dark time" between pulses, the pulsed light beam can result in a lower temperature increase than does the CW light beam. To reduce or minimize the temperature increase of the irradiated portion of the tissue, the temporal pulse width and the duty cycle can be selected to allow a significant portion of the heat generated per pulse to dissipate before the next pulse reaches the irradiated portion. In at least some embodiments, rather than optimizing the beam temporal parameters to minimize the temperature increase, the temporal parameters are selected to effectively correspond to or to be sufficiently close to the timing of the biomolecular processes involved in the absorption of the photons to provide an increased efficacy. Rather than having a temporal pulse width on the order of hundreds of microseconds, at least some embodiments utilize a temporal pulse width, which does not optimize the thermal relaxation of the irradiated tissue (e.g., milliseconds, tens of milliseconds, hundreds of milliseconds). Since these pulse widths are significantly longer than the thermal relaxation time scale, the resulting temperature increases are larger than those of smaller pulse widths, but still less than that of CW light beams due to the heat dissipation the time between the pulses.

A number of studies have investigated the effects of in vitro irradiation of cells using pulsed light on various aspects of the cells. A study of the action mechanisms of incoherent pulsed radiation at a wavelength of 820 nanometers (pulse repetition frequency of 10 Hz, pulse width of 20 milliseconds, dark period between pulses of 80 milliseconds, and duty factor (pulse duration to pulse period ratio) of 20%) on in vitro cellular adhesion has found that pulsed infrared radiation at 820 nanometers increases the cell-matrix attachment. (T. I. Kant et al., "*Cell Attachment to Extracellular Matrices is Modulated by Pulsed Radiation at* 820 nm *and Chemicals that Modify the Activity of Enzymes in the Plasma Membrane*," Lasers in Surgery and Medicine, Vol. 29, pp. 274-281 (2001) which is incorporated in its entirety by reference herein.) It was hypothesized in this study that the modulation of the monovalent ion fluxes through the plasma membrane, and not the release of arachidonic acid, is involved in the cellular signaling pathways activated by irradiation at 820 nanometers. A study of light-induced changes to the membrane conductance of ventral photoreceptor cells found behavior which was dependent on the pulse parameters, indicative of two light-induced membrane processes. (J. E. Lisman et al., "*Two Light-Induced Processes in the Photoreceptor Cells of Limulus Ventral Eye*," J. Gen. Physiology, Vol. 58, pp. 544-561 (1971), which is incorporated in its entirety by reference herein.) Studies of laser-activated electron injection into oxidized cytochrome c oxidase observed kinetics which establishes the reaction sequence of the proton pump mechanism and some of its thermodynamic properties have time constants on the order of a few milliseconds. (I. Belevich et al., "*Exploring the proton pump mechanism of cytochrome c oxidase in real time*," Proc. Nat'l Acad. Sci., Vol. 104, pp. 2685-2690 (2007); I. Belevich et al., "*Proton-coupled electron transfer drives the proton pump of cytochrome c oxidase*," Nature, Vol. 440, pp. 829-832 (2006), both of which are incorporated in its entirety by reference herein.) An in vivo study of neural activation based on pulsed infrared light proposed a photothermal effect from transient tissue temperature changes resulting in direct or indirect activation of transmembrane ion channels causing propagation of the action potential. (J. Wells et al., "*Biophysical mechanisms responsible for pulsed low-level laser excitation of neural tissue*," Proc. SPIE, Vol. 6084, pp. 60840X (2006), which is incorporated in its entirety by reference herein.)

In at least some embodiments, the temporal profile of the pulsed light beam has a peak irradiance, a temporal pulse width, a temporal pulse shape, a duty cycle, and a pulse repetition rate or frequency. In at least some embodiments in which the pulsed light beam is transmitted through a region of the eye, at least one of the peak irradiance, temporal pulse width, temporal pulse shape, duty cycle, and pulse repetition rate or frequency is selected to provide a time-averaged irradiance (averaged over a time period including a plurality of pulses) at the emission surface of the light source between 0.01 mW/cm$^2$ to 1 W/cm$^2$, between 10 mW/cm$^2$ to 10 W/cm$^2$, between 100 mW/cm$^2$ to 1000 mW/cm$^2$, between 500 mW/cm$^2$ to 1 W/cm$^2$, or between 650 mW/cm$^2$ to 750 mW/cm$^2$ across the cross-sectional area of the light beam. In at least some embodiments, the time-averaged irradiance at the retinal tissue being treated is greater than 0.01 mW/cm$^2$.

In at least some embodiments, the temporal pulse shape is generally rectangular, generally triangular, or any other shape. In at least some embodiments, the pulses have a rise time (e.g., from 10% of the peak irradiance to 90% of the peak irradiance) less than 1% of the pulse ON time, or a fall time (e.g., from 90% of the peak irradiance to 10% of the peak irradiance) less than 1% of the pulse ON time.

In at least some embodiments, the pulses have a temporal pulse width (e.g., pulse ON time) in a range between 0.001 millisecond and 150 seconds, between 0.01 millisecond and 10 seconds, between 0.1 millisecond and 1 second, between 0.5 millisecond and 100 milliseconds, between 2 milliseconds and 20 milliseconds, or between 1 millisecond and 10 milliseconds. In at least some embodiments, the pulse width is 0.5, 1, 2, 4, 6, 8, 10, 15, 20, 30, 40, 50, 60, 70, 80, 90, 100, 120, 140, 160, 180, 200, 220, 240, 260, 280, or 300 milliseconds. In at least some embodiments, the temporal pulse width is in a range between 0.1 milliseconds and 150 seconds.

In at least some embodiments, the time between pulses (e.g., pulse OFF time) is in a range between 0.01 millisecond and 150 seconds, between 0.1 millisecond and 100 milliseconds, between 4 milliseconds and 1 second, between 8 milliseconds and 500 milliseconds, between 8 milliseconds and 80 milliseconds, or between 10 milliseconds and 200 milliseconds. In at least some embodiments, the time between pulses is 4, 8, 10, 20, 50, 100, 200, 500, 700, or 1000 milliseconds.

In at least some embodiments, the pulse duty cycle is in a range between 1% and 80% or in a range between 10% and 30%. In at least some embodiments, the pulse duty cycle is 10%, 20%, 30%, 40%, 50%, 60%, 70%, 80%, or 90%.

In at least some embodiments, the peak irradiance per pulse, or pulse energy density, across the cross-sectional area of the light beam at the emission surface of the light source is in a range between 0.01 mW/cm$^2$ to 1 W/cm$^2$, between 10 mW/cm$^2$ to 10 W/cm$^2$, between 100 mW/cm$^2$ to 1000 mW/cm$^2$, between 500 mW/cm$^2$ to 1 W/cm$^2$, between 650 mW/cm$^2$ to 750 mW/cm$^2$, between 20 mW/cm$^2$ to 20 W/cm$^2$, between 200 mW/cm$^2$ to 2000 mW/cm$^2$, between 1 W/cm$^2$ to 2 W/cm$^2$, between 1300 mW/cm$^2$ to 1500 mW/cm$^2$, between 1 W/cm$^2$ to 1000 W/cm$^2$, between 10 W/cm$^2$ to 100 W/cm$^2$, between 50 W/cm$^2$ to 100 W/cm$^2$, or between 65 W/cm$^2$ to 75 W/cm$^2$.

In at least some embodiments, the pulse energy density, or energy density per pulse, can be calculated as the time-averaged power density divided by pulse repetition rate, or frequency. For example, the smallest pulse energy density will happen at the smallest average power density and fastest pulse repetition rate, where the pulse repetition rate is duty cycle divided by the temporal pulse width, and the largest pulse energy density will happen at the largest average power density and slowest pulse repetition rate. For example, at a time-averaged power density of 0.01 mW/cm$^2$ and a frequency of 100 kHz, the pulse energy density is 0.1 nJ/cm$^2$ and at a time-averaged power density of 10 W/cm$^2$ and a frequency of 1 Hz, the pulse energy density is 10 J/cm$^2$. As another example, at a time-averaged power density of 10 mW/cm$^2$ and a frequency of 10 kHz, the pulse energy density is 1 µJ/cm$^2$ As yet another example, at a time-averaged power density of 700 mW/cm$^2$ and a frequency of 100 Hz, the pulse energy density is 7 mJ/cm$^2$.

Beam Size and Beam Profile

In at least some embodiments, the light beam emitted from the light source has a nominal diameter in a range of 10 millimeters to 40 millimeters, in a range of 20 millimeters to 35 millimeters, or equal to 30 millimeters. In at least some embodiments, the cross-sectional area is generally circular with a radius in a range of 1 centimeter to 2 centimeters. In at least some embodiments, the light beam emitted from the emission surface has a cross-sectional area greater than 2 cm$^2$ or in a range of 2 cm$^2$ to 20 cm$^2$ at the emission surface of the light source.

Eyebox or Eyepiece

The beam diameter can be defined as the largest chord of the perimeter of the area of the eye irradiated by the light beam at an intensity of at least $1/e^2$ of the maximum intensity of the light beam. In at least some embodiments, the perimeter of the light beam used to determine the diameter of the beam can be defined to be those points at which the intensity of the light beam is $1/e^2$ of the maximum intensity of the light beam. In at least some embodiments, the maximum-useful diameter is limited by the size of the subject's orbital area and by the heating of the subject's orbital area by the irradiation. In at least some embodiments, the minimum-useful diameter is limited by heating and by the total number of treatment sites that could be practically implemented. For example, to cover the subject's eye with a beam having a small beam diameter would correspondingly use a large number of treatment sites. In at least some embodiments, the time of irradiation per treatment site can be adjusted accordingly to achieve a desired exposure dose.

Specifying the total flux inside a circular aperture with a specified radius centered on the exit aperture ("encircled energy") is a method of specifying the power (irradiance) distribution over the light beam emitted from the emission surface. The "encircled energy" can be used to ensure that the light beam is not too concentrated, too large, or too small. In at least some embodiments, the light beam emitted from the emission surface has a total radiant power, and the light beam has a total flux inside a 20-millimeter diameter cross-sectional circle centered on the light beam at the emission surface which is no more than 75% of the total radiant power. In at least some embodiments, the light beam has a total flux inside a 26-millimeter diameter cross-sectional circle centered on the light beam at the emission surface, which is no less than 50% of the total radiant power.

In at least some embodiments, the beam intensity profile has a semi-Gaussian profile, while in at least some embodiments, the beam intensity profile has a "top hat" profile. In at least some embodiments, the light beam is substantially without high flux regions or "hot spots" in the beam intensity profile in which the local flux, averaged over a 3 millimeter by 3 millimeter area, is more than 10% larger than the average flux. In at least some embodiments, the device advantageously generate a light beam substantially without hot spots, thereby avoiding large temperature gradients, which would otherwise cause discomfort to the subject.

Divergence

In at least some embodiments, the beam divergence emitted from the emission surface is significantly less than the scattering angle of light inside the body tissue being irradiated, which is typically several degrees. In at least some embodiments, the light beam has a divergence angle greater than zero and less than 35 degrees.

Total Treatment Time

The total treatment time can be controlled by the programmable controller. The real time clock and the timers of the programmable controller can be used to control the timing of a particular therapeutic regimen and to allow for scheduled treatment (such as daily, twice a day, or every other day). In at least some embodiments, the treatment proceeds continuously for a period of 10 seconds to 2 hours, for a period of 1 to 20 minutes, or for a period of 1 to 5 minutes. For example, the total treatment time in at least some embodiments is two minutes. In at least some embodiments, the light energy is delivered for at least one total treatment period of at least five minutes per eye, or for at least one total treatment period of at least ten minutes for both eyes. The minimum treatment time of at least some embodiments is limited by the biological response time (which is on the order of microseconds). The maximum treatment time of at least some embodiments can be limited by heating and by practical treatment times (e.g., completing treatment within about 24 hours of injury). The light energy can be pulsed during the treatment period or the light energy can be continuously applied during the treatment period. If the light is pulsed, the pulses can be 2 milliseconds long and occur at a frequency of 100 Hz or at least 10 nanoseconds long and occur at a frequency of up to 100 kHz, although shorter or longer pulse widths or lower or higher frequencies can be used. For example, the light can be pulsed at a frequency of 1 Hz to 100 Hz, from 100 Hz to 1 kHz, from 1 kHz to 100 kHz, less than 1 Hz, or greater than 100 kHz.

In at least some embodiments, the treatment may be terminated after one treatment period, while in other embodiments, the treatment may be repeated for at multiple treatment periods. The time between subsequent treatment periods can be at least five minutes, at least two in a 24-hour period, at least 1 to 2 days, or at least one week. The treatment can be repeated multiple times per day or multiple times per week. The length of treatment time and frequency of treatment periods can depend on several factors, including the functional recovery of the subject and the results of imaging analysis of the injury, the disease or condition being treated, the use of pulsed or continuous light, the irradiance of the light, the number of light sources used, or the sequence or pattern of the treatment. In at least some embodiments, the timing parameters can be adjusted in response to a feedback signal from a sensor or other device (e.g., biomedical sensor, magnetic resonance imaging device) monitoring the subject.

Transmission in Human Eye

In at least some embodiments, fluences of red or NIR as low as 3 to 5 J/cm$^2$ will be beneficial in vivo, but a large dose like 50 to 100 J/cm$^2$ may lose the beneficial effect.

The explanations and illustrations presented herein are intended to acquaint others skilled in the art with the present disclosure, its principles, and its practical application. Those skilled in the art may adapt and apply the present disclosure in its numerous forms, as may be best suited to the requirements of a particular use. Accordingly, the specific embodiments of the present present disclosure as set forth are not intended as being exhaustive or limiting of the present disclosure.

Conditional language, for example, among others, "can," "could," "might," or "may," unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without user input or prompting, whether these features, elements or steps are included or are to be performed in any particular embodiment.

While the present disclosure has been discussed in the context of certain embodiments and examples, it should be appreciated that the present present disclosure extends beyond the specifically disclosed embodiments to other alternative embodiments or uses of the present disclosures and obvious modifications and equivalents thereof. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, or rearranged. Additionally, the skilled artisan will recognize that any of the above-described methods can be carried out using any appropriate apparatus. Further, the disclosure herein of any particular feature, aspect, method, property, characteristic, quality, attribute, element, or the like in connection with various embodiments can be used in all other embodiments set forth herein. Additionally, processing steps may be added, removed, or reordered. A wide variety of designs and approaches are possible.

For purposes of this disclosure, certain aspects, advantages, and novel features of the present disclosure are described herein. It is to be understood that not necessarily all such advantages may be achieved in accordance with any particular embodiment of the present disclosure. Thus, for example, those skilled in the art will recognize that the present disclosure may be embodied or carried out in a manner that achieves one advantage or group of advantages as taught herein without necessarily achieving other advantages as may be taught or suggested herein.

What is claimed is:

1. A self-standing device for delivery of photobiomodulation (PBM) to retinal tissue of an eye of a patient, the device comprising:

a housing comprising an interior;

an eyepiece or eyebox configured and arranged for placement of an eye of the patient adjacent the eyepiece or eyebox;

a first light source selected from one or more LED, lamp, or laser, or any combination thereof, wherein the first light source is configured to produce a first light beam having a first therapeutic wavelength, and wherein the first light source is disposed within the housing;

a second light source selected from one or more LED, lamp, or laser, or any combination thereof, wherein the second light source is configured to produce a second light beam having a second therapeutic wavelength, wherein the second light source is separate from the first light source and is disposed within the housing, and wherein the second therapeutic wavelength differs from the first therapeutic wavelength by at least 25 nm;

a programmable controller operatively coupled to the first light source and to the second light source, wherein the programmable controller is configured to direct the first light source and the second light source to produce the first light beam and the second light beam, respectively, wherein directing the first light source and the second light source comprises controlling one or more PBM parameter selected from a light energy emission, a light energy density, a light energy duration, a light energy frequency, a light energy area, or a light energy sequence, or any combination thereof, of the light beams produced by the first and the second light sources;

an aperture disposed within the housing, wherein the device is configured and arranged to direct the first light beam and the second light beam through the aperture and through the eyepiece or eyebox to provide PBM to the retinal tissue of the patient;

a relay structure configured and arranged to receive the first light beam and the second light beam from the aperture and direct the first light beam and the second light beam to the eyepiece or eyebox;

an actuator configured and arranged to move at least a portion of the relay structure to change a direction of the first light beam and the second light beam from at least a first position to at least a second position; and a patient interface surface for positioning the patient to receive the PBM, wherein the patient interface surface comprises a chin rest, a forehead rest, or both.

2. The device of claim 1, further comprising a third light source producing a third light beam having a third therapeutic wavelength, wherein the third light source is disposed within the housing, and wherein the third therapeutic wavelength differs from each of the first therapeutic wavelength and the second therapeutic wavelength by at least 25 nm.

3. The device of claim 1, wherein the first light source is configured and arranged to emit a pulsed light beam comprising a plurality of pulses having a temporal pulse width, wherein the temporal pulse width is in a range from 0.1 milliseconds to 150 seconds.

4. The device of claim 1, further comprising a biomedical sensor operatively coupled to the programmable controller and configured to provide real-time feedback information regarding the patient's eye.

5. The device of claim 4, wherein the programmable controller is configured and arranged to regulate emission of light from the first light source and the second light source in accordance with the feedback information.

6. The device of claim 1, wherein the first therapeutic wavelength is in a range from 800 to 900 nm and the second therapeutic wavelength is in a range from 600 to 700 nm.

7. The device of claim 1, wherein the first therapeutic wavelength is in a range from 800 to 900 nm and the second therapeutic wavelength is in a range from 550 to 650 nm.

8. The device of claim 1, further comprising a user interface selected from (i) a touchscreen interface or (ii) a keyboard and display, wherein the user interface is operably coupled to the programmable controller.

9. The device of claim device of claim 1, further comprising one or both of (i) a camera and (ii) a pupil tracking sensor to observe the patient's eye.

10. The device of claim 1, further comprising a beam positioning mechanism operably coupled to the actuator.

11. The device of claim 10, wherein the beam positioning mechanism comprises one or more of a joystick, a trackball, or a touchscreen.

12. A self-standing device for delivery of photobiomodulation (PBM) to retinal tissue of a patient, the device comprising:

a housing comprising an interior;

an eyepiece or eyebox configured and arranged for placement of an eye of the patient adjacent the eyepiece or eyebox;

a first light source selected from one or more LED, lamp, or laser, or any combination thereof, wherein the first light source is configured to produce a first light beam having a first therapeutic wavelength, and wherein the first light source is disposed within the housing;

a second light source selected from one or more LED, lamp, or laser, or any combination thereof, wherein the second light source is configured to produce a second light beam having a second therapeutic wavelength, wherein the second light source is separate from the first light source and is disposed within the housing, and wherein the second therapeutic wavelength differs from the first therapeutic wavelength by at least 25 nm;

a programmable controller operatively coupled to the first light source and to the second light source, wherein the programmable controller is configured to direct the first light source and the second light source to produce the first light beam and the second light beam, respectively, wherein directing the first light source and the second light source comprises controlling one or more PBM parameter selected from a light energy emission, a light energy density, a light energy duration, a light energy frequency, a light energy area, or a light energy sequence, or any combination thereof, of the light beams produced by the first and the second light sources;

a reflective filter disposed within the housing and configured and arranged to substantially pass light having the first therapeutic wavelength and substantially reflect light having the second therapeutic wavelength, wherein the device is configured and arranged to direct the first and second light beams to the reflective filter and then through an aperture disposed within the housing and through the eyepiece or eyebox to provide PBM to the retinal tissue of the patient;

a relay structure configured and arranged to receive the first light beam and the second light beam from the aperture and direct the first light beam and the second light beam to the eyepiece or eyebox;

an actuator configured and arranged to move at least a portion of the relay structure to change a direction of the first light beam and the second light beam from at least a first position to at least a second position; and a patient interface surface for positioning the patient to receive the PBM, wherein the patient interface surface comprises a chin rest, a forehead rest, or both.

13. The device of claim 12, further comprising a biomedical sensor operatively coupled to the programmable controller and configured to provide real-time feedback information regarding the patient's eye.

14. The device of claim 11, wherein the first therapeutic wavelength is in a range from 800 to 900 nm and the second therapeutic wavelength is in a range from 600 to 700 nm.

15. The device of claim 11, wherein the first therapeutic wavelength is in a range from 800 to 900 nm and the second therapeutic wavelength is in a range from 550 to 650 nm.

16. A method of providing photobiomodulation (PBM) to retinal tissue of a patient using the device of claim 1, the method comprising:
placing at least one eye of the patient at the eyepiece or eyebox of the device; and
directing light of at least one of the first therapeutic wavelength or the second therapeutic wavelength from the device to the at least one eye of the patient.

17. The method of claim 16, wherein directing light comprises directing light of at least one of the first therapeutic wavelength or the second therapeutic wavelength from the device through an eyelid of the patient to retinal tissue of the at least one eye of the patient.

18. The method of claim 16, wherein directing light comprises directing light of the first therapeutic wavelength and light of the second therapeutic wavelength from the device through an eyelid of the patient to retinal tissue of the at least one eye of the patient.

19. The method of claim 18, wherein directing light of the first therapeutic wavelength and light of the second therapeutic wavelength comprises sequentially directing the light of the first therapeutic wavelength and the light of the second therapeutic wavelength from the device through the eyelid of the patient to the retinal tissue of the at least one eye of the patient.

20. The method of claim 18, wherein directing light of the first therapeutic wavelength and light of the second therapeutic wavelength comprises simultaneously directing the light of the first therapeutic wavelength and the light of the second therapeutic wavelength from the device through the eyelid of the patient to the retinal tissue of the at least one eye of the patient.

* * * * *